US011691005B2

United States Patent
Erturk

(10) Patent No.: US 11,691,005 B2
(45) Date of Patent: Jul. 4, 2023

(54) MEDICAL DEVICE AND MRI SYSTEMS

(71) Applicant: Medtronic, Inc., Minneapolis, MN (US)

(72) Inventor: Mehmet Arcan Erturk, St. Louis Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 1070 days.

(21) Appl. No.: 16/228,101

(22) Filed: Dec. 20, 2018

(65) Prior Publication Data
US 2020/0197695 A1    Jun. 25, 2020

(51) Int. Cl.
| | | |
|---|---|---|
| *A61N 1/08* | (2006.01) | |
| *A61B 5/055* | (2006.01) | |
| *G01R 33/54* | (2006.01) | |
| *A61N 1/05* | (2006.01) | |
| *A61N 1/36* | (2006.01) | |

(52) U.S. Cl.
CPC .............. *A61N 1/086* (2017.08); *A61B 5/055* (2013.01); *A61N 1/0534* (2013.01); *A61N 1/36142* (2013.01); *G01R 33/543* (2013.01)

(58) Field of Classification Search
CPC .. A61N 1/086; A61N 1/0534; A61N 1/36142; A61N 1/3718; A61N 1/3706; A61B 5/055; A61B 2090/374; G01R 33/543; G01R 33/288; G01R 33/285; G01R 19/0084; G01R 19/0092
See application file for complete search history.

(56) References Cited

U.S. PATENT DOCUMENTS

| | | | | |
|---|---|---|---|---|
| 5,730,134 | A | * | 3/1998 | Dumoulin .......... G01R 33/4804 600/549 |
| 8,041,410 | B2 | | 10/2011 | Zeijlemaker |
| 8,200,334 | B1 | * | 6/2012 | Min .................... A61B 5/02055 607/27 |
| 8,319,496 | B2 | | 11/2012 | Eryaman et al. |
| 8,565,874 | B2 | | 10/2013 | Stubbs et al. |
| 9,381,371 | B2 | | 7/2016 | Stubbs et al. |
| 9,417,298 | B2 | | 8/2016 | Guerin et al. |
| 9,450,306 | B1 | * | 9/2016 | Ebnabbasi ............... H01Q 7/00 |

(Continued)

FOREIGN PATENT DOCUMENTS

| | | | | |
|---|---|---|---|---|
| WO | WO-2018192233 A1 | * | 10/2018 | ............. A61B 5/055 |
| WO | WO-2020107944 A1 | * | 6/2020 | ............. G01R 33/48 |

OTHER PUBLICATIONS

Park, S.-M., Kamondetdacha, R. and Nyenhuis, J.A. (2007), Calculation of MRI-induced heating of an implanted medical lead wire with an electric field transfer function. J. Magn. Reson. Imaging, 26: 1278-1285. (Year: 2007).*

*Primary Examiner* — Colin T. Sakamoto
*Assistant Examiner* — Tommy T Ly
(74) *Attorney, Agent, or Firm* — Shumaker & Sieffert, P.A.

(57) ABSTRACT

In some examples, a method including detecting, via processing circuitry, an induced voltage in at least one of an electrode or a lead conductor of an implantable medical device, wherein the induced voltage is induced in the at least one of the electrode or the lead conductor of the implantable medical device by a radio frequency (RF) field generated by a magnetic resonance imaging (MRI) scanner; and modifying, via the processing circuitry, an MRI scan based on the detected induced voltage.

23 Claims, 19 Drawing Sheets

(56) References Cited

U.S. PATENT DOCUMENTS

| | | | |
|---|---|---|---|
| 2006/0293591 A1* | 12/2006 | Wahlstrand | A61N 1/3706 600/423 |
| 2007/0233195 A1* | 10/2007 | Wahlstrand | G01R 33/56572 607/2 |
| 2007/0265685 A1* | 11/2007 | Zeijlemaker | A61B 5/06 607/60 |
| 2011/0066028 A1* | 3/2011 | Min | G01R 33/288 607/119 |
| 2011/0144524 A1* | 6/2011 | Fish | A61B 34/25 606/41 |
| 2011/0148411 A1* | 6/2011 | Bottomley | G01R 33/58 324/309 |
| 2011/0160791 A1* | 6/2011 | Ellingson | A61N 1/3718 607/27 |
| 2016/0199639 A1* | 7/2016 | Stem | A61N 1/08 607/63 |
| 2017/0303813 A1* | 10/2017 | Lattanzi | A61B 5/0013 |

* cited by examiner

MEDICAL DEVICE AND MRI SYSTEMS

TECHNICAL FIELD

The present disclosure relates to medical device and magnetic resonance imaging systems.

BACKGROUND

Medical devices may be used to treat a variety of medical conditions. Medical electrical stimulation devices, for example, may deliver electrical stimulation therapy to a patient via implanted electrodes. Electrical stimulation therapy may include stimulation of nerve, muscle, or brain tissue, or other tissue within a patient. An electrical stimulation device may be fully implanted within the patient. For example, an electrical stimulation device may include an implantable electrical stimulation generator and one or more implantable leads carrying electrodes.

SUMMARY

The present disclosure relates to implantable medical devices and magnetic resonance imaging (MRI) systems. An MRI system may be configured to perform an MRI scan on a patient having an implantable medical device (IMD). In some examples, the IMD may be configured to sense a voltage induced in the IMD by an MRI system. For example, the sensed voltage may be induced in one or more electrodes and/or conductive leads of the IMD by the MRI system as a result of electric fields produced by RF excitation during an MRI scan by an MRI scanner. Such RF excitation may cause heating of the electrode(s) and/or conductive lead(s) during an MRI scan. The implantable medical device may sense the induced voltage using sensing circuitry that is also used by the IMD to sense other electrical signals in the patient during the normal operation of the IMD outside of an MRI scan.

The system may use the sensed induced voltage as a marker to predict or estimate heating of the implantable medical device during an MRI scan. In some examples, the system may predict the heating of the IMD for a plurality of different MRI scan settings based on a sensed induced voltage for each setting and identify one or more MRI scan settings (e.g., shimming settings) that provide for a relatively low level of heating during an MRI scan, e.g., as compared to the heating predicted for other available MRI scan settings. For example, the system may select MRI scan settings that provide for an electric field distribution for the MRI scan that causes a relatively low level of heating during an MRI scan while also having a desirable magnetic field distribution for the MRI scan.

Additionally, or alternatively, the system may estimate the heating of the IMD based on a sensed induced voltage during an MRI scan to determine the time duration of the MRI scan, power of the MRI scan and/or other MRI scan parameters, e.g., while still maintaining the estimated temperature of the IMD during the scan below a threshold temperature. In some examples, the system may utilize the sensed induced voltage to estimate the temperature of the electrode(s) and/or lead conductor(s) of the IMD in approximately real-time during an MRI scan and adjust one or more MRI scan parameters during the scan based on the estimated temperature. For example, the system may terminate the MR scan or otherwise modify one or more parameters of the MRI scan based on such an estimated temperature of the electrode(s) and/or lead conductor(s) of the IMD during the MRI scan.

In one example, the disclosure relates to a method comprising detecting, via processing circuitry, an induced voltage in at least one of an electrode or a lead conductor of an implantable medical device, wherein the induced voltage is induced in the at least one of the electrode or the lead conductor of the implantable medical device by a radio frequency (RF) field generated by a magnetic resonance imaging (MRI) scanner; and modifying, via the processing circuitry, an MRI scan based on the detected induced voltage.

In another example, the disclosure relates to a system comprising an implantable medical device; a magnetic resonance imaging (MRI) scanner; and processing circuitry, wherein the implantable medical device is configured to detect an induced voltage in at least one of an electrode or a lead conductor of the implantable medical device, wherein the induced voltage is induced in the at least one of the electrode or the lead conductor of the implantable medical device by a radio frequency (RF) field generated by a magnetic resonance imaging (MRI) scanner, and modify an MRI scan based on the detected induced voltage.

In another example, the disclosure relates to a method comprising sensing, via an implantable medical device, an induced voltage in at least one of an electrode or a lead conductor of the implantable medical device, wherein the induced voltage is induced in the at least one of the electrode or the lead conductor of the implantable medical device by a radio frequency (RF) field generated by a magnetic resonance imaging (MRI) scanner; and transmitting, from the implantable medical device to an MRI device, at least one of voltage information defined by the sensed induced voltage information or control information including instructions for controlling the MRI scanner to deliver an MRI scan based on the sensed induced voltage.

In another examples, the disclosure relates to a system comprising an implantable medical device; and processing circuitry, wherein the processing circuitry is configured to sense, via the implantable medical device, an induced voltage in at least one of an electrode or a lead conductor of the implantable medical device, wherein the induced voltage is induced in the at least one of the electrode or the lead conductor of the implantable medical device by a radio frequency (RF) field generated by a magnetic resonance imaging (MRI) scanner, and transmit, from the implantable medical device to an MRI device, at least one of voltage information defined by the sensed induced voltage information or control information including instructions for controlling the MRI scanner to deliver an MRI scan based on the sensed induced voltage.

The details of one or more aspects of the disclosure are set forth in the accompanying drawings and the description below. Other features, objects, and advantages will be apparent from the description and drawings, and from the claims.

DETAILED DESCRIPTION

Figure 1:
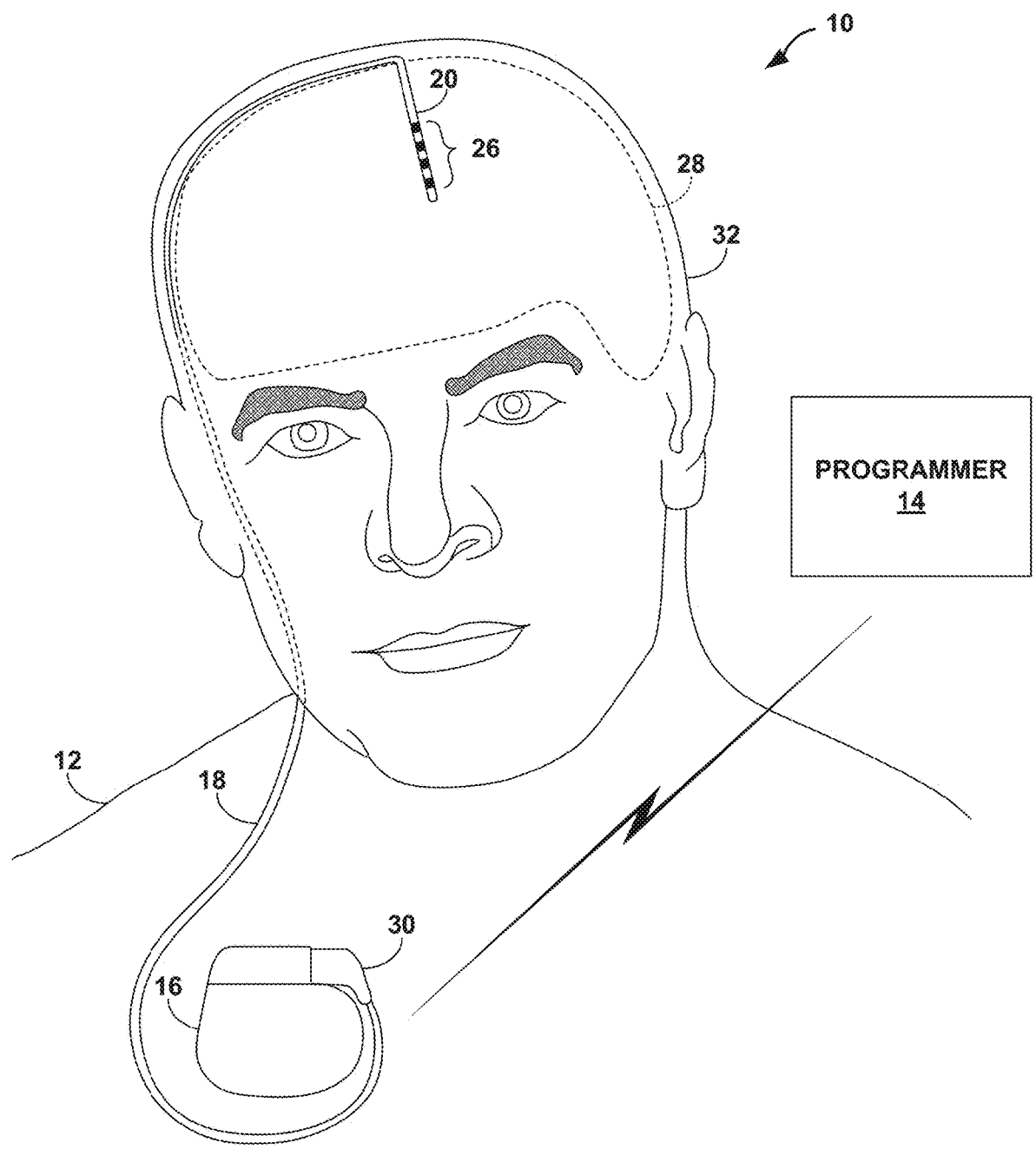
FIG. 1 is a conceptual diagram illustrating an example medical device system.

As described above, some examples of the disclosure are directed to medical device systems and techniques involving magnetic resonance imaging (MRI) scans. MRI has been developed as an imaging technique adapted to obtain both images of anatomical features of human patients as well as some aspects of the functional activities of biological tissue. These images may have medical diagnostic value, e.g., in determining the state of the health of the tissue examined.

In a magnetic-resonance imaging process, a patient is typically aligned to place the portion of the patient's anatomy to be examined in the imaging volume of the magnetic-resonance imaging apparatus. Such an MRI device may comprise a primary magnet for supplying a constant magnetic field ($B_0$) which, by convention, may be along the z-axis and may be substantially homogeneous over the imaging volume and secondary magnets that can provide linear magnetic field gradients along each of three principal Cartesian axes in space (e.g., x, y, and z, or x1, x2 and x3, respectively). A magnetic field gradient ($\Delta B_0/\Delta xi$) refers to the variation of the field along the direction parallel to $B_0$ with respect to each of the three principal Cartesian axes, xi. The MRI device may also comprise one or more radio-frequency (RF) coils, which provide excitation signals to the patient's body, placed in the imaging volume in the form of a pulsed rotating magnetic field. This field is may be referred to as the scanner's "B1" field and as the scanner's "RF" or "radio-frequency" field. The frequency of the excitation signals may be the frequency at which this magnetic field rotates. These coils may also be used for detection of the excited patient's body material magnetic-resonance imaging response signals.

The presence of an IMD having one or more electrically conductive portions within a patient undergoing MRI may present one or more undesired issues. For example, an IMD, such as, an implantable cardiac device (ICD) or implantable neurostimulator (INS) may have one or more electrically conductive leads that allow the IMD to conduct electrical signals to and/or from electrodes located on the lead(s). RF excitation during MRI may generate magnetic fields to tilt the spins from equilibrium to produce MRI signals. Electric fields produced during MRI RF excitation may couple to the conductive leads of the IMD, which act as an antenna, and may be deposited at conductor/tissue interface (e.g., the electrode surface), causing local temperature elevations and potential tissue damage. In some examples, this phenomenon may be referred to as "RF lead heating."

As result, in some examples, the power and/or duration of an MRI scan of a patient may be limited due to the presence of an IMD in a patient. In some examples, the power and/or duration of an MRI scan may be kept below a threshold to prevent an undesired amount of RF lead heating during the MRI scan. Without a temperature sensor to monitor the actual temperature increase at the electrode(s) of the IMD during an MRI scan, the maximum power and/or duration of an MRI scan set by a clinician may be relatively low so that the RF heating of the IMD does not increase the temperature of the IMD electrode(s) above a predetermined level. In other examples, a clinician may elect to not perform an MRI scan on a patient with an implanted IMD to prevent the occurrence of such RF heating.

In accordance with examples of the disclosure, a system may be configured to detect a voltage induced in an IMD (e.g., in one or more leads of an IMD) by the RF field of an MRI device and utilize the induced voltage as a marker of RF lead heating of the IMD. The detected induced voltage may reflect the RF coupling of the IMD with the electric fields produced during MRI RF excitation by an MRI scanner.

In some examples, the system may utilize the induced voltage detected during an MRI scan to estimate the temperature of the IMD during the MRI scan, e.g., in real-time during the MRI scan. The system may then control the delivery of the MRI scan based on the estimated temperature of the IMD, e.g., by terminating the delivery of the MRI scan before the estimated temperature increases above a predetermined threshold temperature or adjusting other parameters of the MRI scan as necessary to keep the estimated temperature of the IMD device at or below the threshold level. As will be described in further detail below, in some examples, techniques that utilize induced voltage as an input for estimating IMD temperature during an MRI scan may be more accurate than other techniques for estimating IMD temperature during an MRI scan that do not use induced voltage as an input parameter.

In some examples, the system may use a detected voltage induced by the RF field of an MRI device as a marker to predict RF heating during an MRI scan. For example, prior to performing a full MRI scan on the patient, the system may evaluate one or more MRI scan settings to identify an MRI scan setting that is predicted to result in a desirable level of RF heating. In one example, the system may determine, for each of a plurality of different available MRI scan settings, the voltage induced by the RF field associated with each of the plurality of different available MRI scan settings. In some examples, each of the different MRI scan settings includes a different shimming setting for the RF field of the MRI scan. Each of the MRI scan settings may define a different electric field distribution when used for an MRI scan, which may result in different induced voltage and RF heating of the IMD for each MRI scan setting. To prevent an undesired level of RF heating of an electrode, each of the plurality of different available MRI scan settings may be tested by delivering relatively low power, short duration pulses at each scan setting and then measuring the voltage induced by the relatively low power, short duration pulses at each scan setting. The system may then identify an MRI scan setting that resulted in an induced voltage below a predetermined voltage threshold or the MRI scan setting that resulted in the lowest induced voltage, and perform a full MRI scan on the patient using the identified MRI scan setting. The predetermined voltage threshold may correspond to an induced voltage value that results in an acceptable level of RF heating of the IMD during the MRI scan.

In some examples, the IMD may sense the voltage induced by the RF field of the MRI device in a conductive lead using local field potential (LFP) or other sensing capabilities and hardware otherwise utilized to sense bioelectrical signals within the patient. For example, the IMD may use LFP sensing capabilities outside of an MRI environment to sense bioelectrical brain signals of the patient as part of a deep brain stimulation (DBS) therapy delivered to a patient by the IMD. In this manner, a system may utilize components that are already present in the IMD as part of the therapy delivery function in order to also improve the compatibility of an IMD with an MRI scan, e.g., by detecting the RF energy coupling with the IMD before or during an MRI scan. In other examples, the IMD may include other sensing circuitry configured to sense voltage induced by the RF field of an MRI device that is separate from the LFP or other bioelectrical signal sensing circuitry of the IMD.

In some examples, an MRI scanner may have multi-transmit RF coils and transmit RF field shaping capabilities. The multi-transmit RF coils may be used to tailor magnetic field distributions inside a patient to improve image quality. The multi-transmit RF coils may also be used to change the electric field distribution of an MRI scan to reduce the interactions between an IMD and the transmitted RF field, e.g., to alleviate the risk of RF lead heating. The systems and techniques described herein may be utilized to identify and tailor MRI scan settings in such MRI scanners by sensing the voltage induced by RF field of an MRI scanner and using the induced voltage, e.g., as a marker for RF coupling of the IMD and RF heating of the IMD.

In some examples, the RF energy coupled to the lead or other conductive portion of an IMD, detected in the form of an induced voltage in the IMD, may be used as a marker to predict the risk of RF lead heating. By measuring the RF energy coupled to the lead during various multi-transmit RF excitation modes, a "safe" RF excitation mode (e.g., a RF excitation mode that results in an acceptable level of RF heating of the IMD during an MRI scan) in terms of RF lead heating may be determined. After determining a "safe" RF excitation mode, an MRI scan may be performed, e.g., without the need for restricting MRI sequence parameters. Such an approach may enable full body MRI normal mode labeling for a range of therapies that currently have restrictive MRI labeling (e.g., 2 microTesla limit for some deep brain system (DBS) therapy systems).

FIG. 1 is a conceptual diagram illustrating an example stimulation therapy system with a conductive lead implanted in the brain of a patient. As shown in FIG. 1, system 10 includes IMD 16, lead extension 18, lead 20 and one or more electrodes 26 implanted within patient 12. Specifically, lead 20 enters through cranium 32 and is implanted within brain 28 to deliver DBS. One or more electrodes 26 of lead 20 provides electrical pulses to surrounding anatomical regions of brain 28 in a therapy that may treat or otherwise manage a condition of patient 12. In some examples, more than one lead 20 may be implanted within brain 28 of patient 12 to stimulate multiple anatomical regions of the brain. As shown in FIG. 1, system 10 may also include a programmer 14, which may be a handheld device, portable computer, or workstation that provides a user interface to a clinician. The clinician interacts with the user interface to program stimulation parameters.

For ease of illustration, examples of the disclosure will primarily be described with regard to implantable electrical stimulation leads and implantable medical devices that deliver neurostimulation therapy to a patient's brain in the form of DBS. However, the features and techniques described herein may be useful in other types of systems, including an IMD with one or more conductive leads or other conductive portions. For example, the features and techniques described herein may be used in systems with medical devices that deliver stimulation therapy to a patient's heart, e.g., implantable cardiac devices (ICDs) such as pacemakers, and pacemaker-cardioverter-defibrillators. As other examples, the features and techniques described herein may be embodied in systems that deliver other types of neurostimulation therapy (e.g., spinal cord stimulation, pain stimulation, pelvic floor stimulation, or sacral nerve stimulation), stimulation of at least one muscle or muscle groups, stimulation of at least one organ such as gastric system stimulation, stimulation concomitant to gene therapy, and, in general, stimulation of any tissue of a patient. As other examples, the features and techniques described herein may be embodied in systems that sense electrical signals, such as, bioelectrical signals of the patient.

Therapy system 10 includes medical device programmer 14, IMD 16, lead extension 18, and lead 20 with set of electrodes 26. IMD 16 includes a stimulation therapy module that includes an electrical stimulation generator that generates and delivers electrical stimulation therapy to one or more regions of brain 28 of patient 12 via one or more of electrode 26 of lead 20. In the example shown in FIG. 1, therapy system 10 may be referred to as a DBS system because IMD 16 provides electrical stimulation therapy directly to tissue within brain 28, e.g., a tissue site under the dura mater of brain 28. In other examples, leads 20 may be positioned to deliver therapy to a surface of brain 28 (e.g., the cortical surface of brain 28).

In the example shown in FIG. 1, IMD 16 may be implanted within a subcutaneous pocket above the clavicle of patient 12. In other examples, IMD 16 may be implanted within other regions of patient 12, such as a subcutaneous pocket in the abdomen or buttocks of patient 12 or proximate the cranium of patient 12. Implanted lead extension 18 is coupled to IMD 16 via connector block 30 (also referred to as a header), which may include, for example, electrical contacts that electrically couple to respective electrical contacts on lead extension 18. The electrical contacts electrically couple the electrodes 26 carried by lead 20 to IMD 16. Lead extension 18 traverses from the implant site of IMD 16 within a chest cavity of patient 12, along the neck of patient 12 and through the cranium of patient 12 to access brain 28. Generally, IMD 16 is constructed of a biocompatible material that resists corrosion and degradation from bodily fluids. IMD 16 may comprise a hermetic housing to substantially enclose components, such as a processor, therapy module, and memory.

Lead 20 may be positioned to deliver electrical stimulation to one or more target tissue sites within brain 28 to manage patient symptoms associated with a disorder of patient 12. Lead 20 may be implanted to position electrodes 26 at desired locations of brain 28 through respective holes in cranium 32. Lead 20 may be placed at any location within brain 28 such that electrodes 26 are capable of providing electrical stimulation to target tissue sites within brain 28 during treatment. Although FIG. 1 illustrates system 10 as including one lead 20 coupled to IMD 16 via lead extension 18, in some examples, system 10 may include more than one lead.

Lead 20 may deliver electrical stimulation via electrodes 26 to treat any number of neurological disorders or diseases in addition to movement disorders, such as seizure disorders or psychiatric disorders. Lead 20 may be implanted within a desired location of brain 28 via any suitable technique, such as through respective burr holes in a skull of patient 12 or through a common burr hole in the cranium 32. Lead 20 may be placed at any location within brain 28 such that electrodes 26 of lead 20 are capable of providing electrical stimulation to targeted tissue during treatment. In the examples shown in FIG. 1, electrodes 26 of lead 20 are shown as ring electrodes. In other examples, electrodes 26 of lead 20 may have different configurations including segmented electrodes or paddle electrodes. Electrodes 26 of lead 20 may have a complex electrode array geometry that is capable of producing shaped electrical fields. In this manner, e.g., with segmented electrodes or complex electrode geometries, electrical stimulation may be directed to a specific direction from lead 20 to enhance therapy efficacy and reduce possible adverse side effects from stimulating a large volume of tissue.

IMD 16 may deliver electrical stimulation therapy to brain 28 of patient 12 according to one or more stimulation therapy programs. A therapy program may define one or more electrical stimulation parameter values for therapy generated and delivered from IMD 16 to brain 28 of patient 12. Where IMD 16 delivers electrical stimulation in the form of electrical pulses, for example, the stimulation therapy may be characterized by selected pulse parameters, such as pulse amplitude, pulse rate, and pulse width. In addition, if different electrodes are available for delivery of stimulation, the therapy may be further characterized by different electrode combinations, which can include selected electrodes and their respective polarities. The exact therapy parameter values of the stimulation therapy that helps manage or treat a patient disorder may be specific for the particular target stimulation site (e.g., the region of the brain) involved as well as the particular patient and patient condition.

In addition to delivering therapy to manage a disorder of patient 12, therapy system 10 monitors one or more bioelectrical brain signals of patient 12. For example, IMD 16 may include a sensing module that senses bioelectrical brain signals within one or more regions of brain 28. In the example shown in FIG. 1, the signals generated by electrodes 26 are conducted to the sensing module within IMD 16 via conductors within lead 20 and lead extension 18. In some examples, a processor of IMD 16 may sense the bioelectrical signals within brain 28 of patient 12 and controls delivery of electrical stimulation therapy to brain 28 via electrodes 26. The bioelectrical brain signals monitored by IMD 16 may reflect changes in electrical current produced by the sum of electrical potential differences across brain tissue. Examples of the monitored bioelectrical brain signals include, but are not limited to, an electroencephalogram (EEG) signal, an electrocorticogram (ECoG) signal, a local field potential (LFP) sensed from within one or more regions of a patient's brain and/or action potentials from single cells within the patient's brain.

As will be described further below, IMD 16 may be configured to sense a voltage induced within lead 20, lead extension 18, and/or electrodes 26. The sensed voltage may be induced by the RF fields generated by an MRI scanner, e.g., during an MRI scan. The induced voltage may be a result of coupling of the conductive portions of lead 20, lead extension 18, and/or electrodes 26 to the electric fields produced by the MRI scanner during an MRI scan. Such coupling may result in RF heating during an MRI scan or otherwise in the presence of an RF field generated by an MRI scanner, as described above.

External programmer 14 wirelessly communicates with IMD 16 as needed to provide or retrieve therapy information. Programmer 14 is an external computing device that the user, e.g., the clinician and/or patient 12, may use to communicate with IMD 16. For example, programmer 14 may be a clinician programmer that the clinician uses to communicate with IMD 16 and program one or more therapy programs for IMD 16. Alternatively, programmer 14 may be a patient programmer that allows patient 12 to select programs and/or view and modify therapy parameters. The clinician programmer may include more programming features than the patient programmer. In other words, more complex or sensitive tasks may only be allowed by the clinician programmer to prevent an untrained patient from making undesired changes to IMD 16.

Programmer 14 may be a hand-held computing device with a display viewable by the user and an interface for providing input to programmer 14 (i.e., a user input mechanism). In other examples, programmer 14 may be a larger workstation or a separate application within another multi-function device, rather than a dedicated computing device. For example, the multi-function device may be a notebook computer, tablet computer, workstation, cellular phone, personal digital assistant or another computing device that may run an application that enables the computing device to operate as a secure medical device programmer 14.

Figure 2:
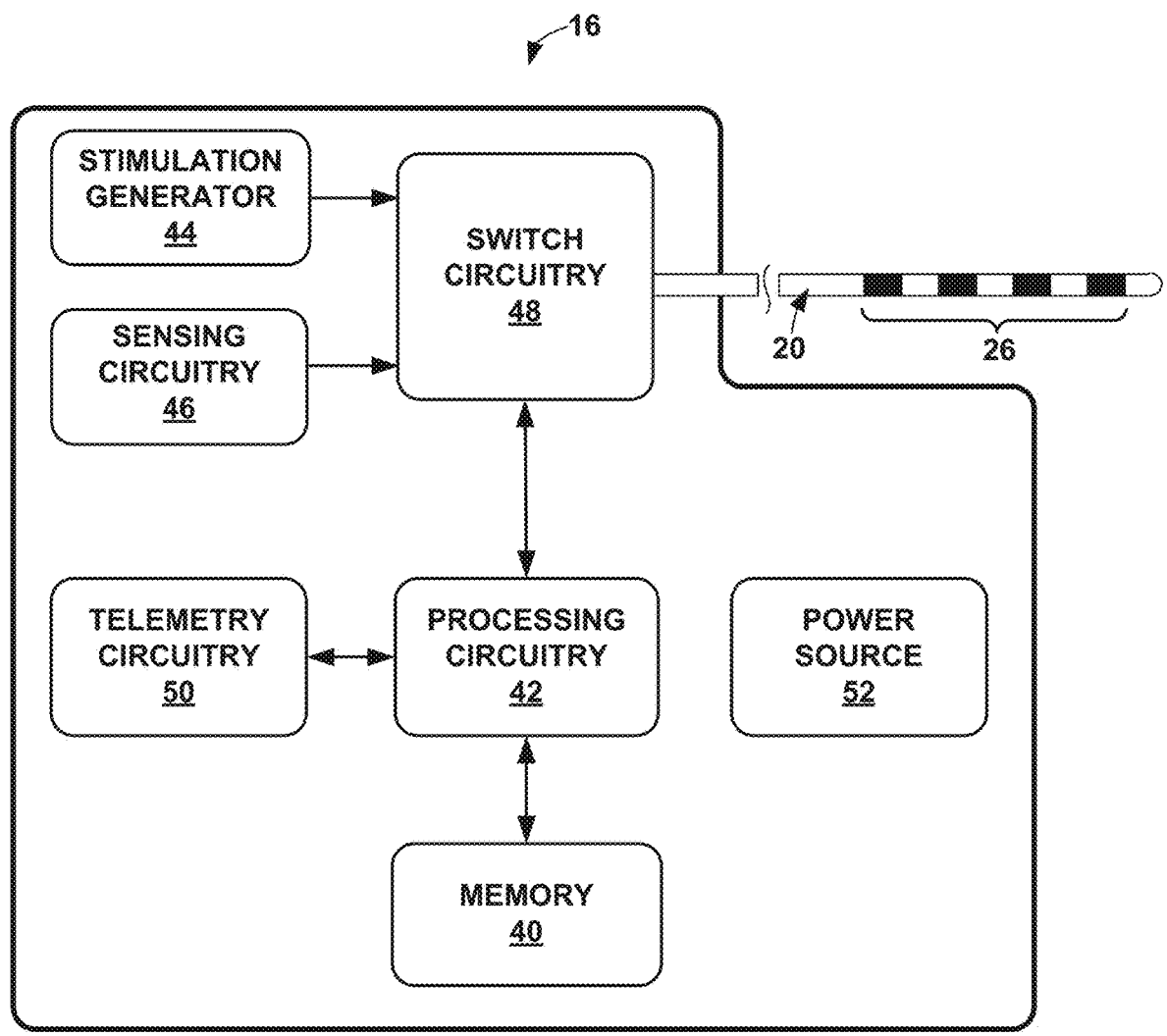
FIG. 2 is a conceptual diagram illustrating the example implantable medical device of shown in FIG. 1.

FIG. 2 is a functional block diagram illustrating components of IMD 16. In the example shown in FIG. 2, IMD 16 includes memory 40, processing circuitry 42, stimulation generator 44, sensing circuitry 46, switch circuitry 48, telemetry circuitry 50, and power source 52. Processing circuitry 42 may include any one or more microprocessors, controllers, digital signal processors (DSPs), application specific integrated circuits (ASICs), field-programmable gate arrays (FPGAs), or discrete logic circuitry. The functions attributed to processors described herein, including processing circuitry 42, may be provided by processing circuitry of a hardware device, e.g., as supported by software and/or firmware.

In the example shown in FIG. 2, sensing circuitry 46 may sense bioelectrical brain signals of patient 12 via select combinations of electrodes 26. The output of sensing circuitry 46 may be received by processing circuitry 42. In some cases, processing circuitry 42 may apply additional processing to the bioelectrical signals, e.g., convert the output to digital values for processing and/or amplify the bioelectrical brain signal. In addition, in some examples, sensing circuitry 46 or processing circuitry 42 may filter the signal from the selected electrodes 26 in order to remove undesirable artifacts from the signal, such as noise from cardiac signals generated within the body of patient 12. Although sensing circuitry 46 is incorporated into a common outer housing with stimulation generator 44 and processing circuitry 42 in FIG. 2, in other examples, sensing circuitry 46 is in a separate outer housing from the outer housing of IMD 16 and communicates with processing circuitry 42 via wired or wireless communication techniques. In some examples, sensing circuitry 46 may sense brain signals substantially at the same time that IMD 16 delivers therapy to patient 14. In other examples, sensing circuitry 46 may sense brain signals and IMD 16 may deliver therapy at different times.

As described herein, sensing circuitry 46 may sense a voltage induced within lead 20, lead extension 18, and/or electrodes 26 by the scanner of an MRI device. The sensed voltage may be induced by the RF fields generated by the MRI scanner, e.g., during an MRI scan. The induced voltage may be a result of coupling of the conductive portions of lead 20, lead extension 18, and/or electrodes 26 to the electric fields produced by the MRI scanner during an MRI scan. Such coupling may result in RF heating during an MRI scan or otherwise in the presence of an RF field generated by an MRI scanner, as described above. As used herein, a lead conductor may refer to one or more electrical conductors of lead 20 and/or lead extension 18 which electrically couple electrodes 26 to one or more components of IMD 16, such as, processing circuitry 42, sensing circuitry 46, simulation generator 44 and/or the like.

Memory 40 may include any volatile or non-volatile media, such as a random access memory (RAM), read only memory (ROM), non-volatile RAM (NVRAM), electrically erasable programmable ROM (EEPROM), flash memory, and the like. Memory 40 may store computer-readable instructions that, when executed by processing circuitry 42, cause IMD 16 to perform various functions described herein. Memory 40 may be considered, in some examples, a non-transitory computer-readable data storage medium comprising instructions that cause one or more processors, such as, e.g., processing circuitry 42, to implement one or more of the example techniques described in this disclosure. The term "non-transitory" may indicate that the data storage medium is not embodied in a carrier wave or a propagated signal. However, the term "non-transitory" should not be interpreted to mean that memory 40 is non-movable. As one example, memory 40 may be removed from IMD 16, and moved to another device. In certain examples, a non-transitory storage medium may store data that can, over time, change (e.g., in RAM).

In the example shown in FIG. 2, processing circuitry 42 controls switch circuitry 48 to sense bioelectrical brain signals with selected combinations of electrodes 26. For example, switch circuitry 48 may create or cut off electrical connections between sensing circuitry 46 and selected electrodes 26 in order to selectively sense bioelectrical brain signals, e.g., in particular portions of brain 28 of patient 12. Processing circuitry 42 may also control switch circuitry 48 to apply stimulation signals generated by stimulation generator 44 to selected combinations of electrodes 26. In particular, switch circuitry 48 may couple stimulation signals to selected conductors within leads 20, which, in turn, deliver the stimulation signals across selected electrodes 26. Switch circuitry 48 may be a switch array, switch matrix, multiplexer, or any other type of switching module configured to selectively couple stimulation energy to selected electrodes 26 and to selectively sense bioelectrical brain signals with selected electrodes 26. Hence, stimulation generator 44 is coupled to electrodes 26 via switch circuitry 48 and conductors within leads 20. In some examples, however, IMD 16 does not include switch circuitry 48. In some examples, IMD 16 may include separate current sources and sinks for each individual electrode (e.g., instead of a single stimulation generator) such that switch circuitry 48 may not be necessary.

Processing circuitry 42 may also control switch circuitry 48 to sense a voltage induced in lead 20, lead extension 18, and/or electrodes 26, e.g., by RF fields generated by an MRI scanner. For example, switch circuitry 48 may create or cut off electrical connections between sensing circuitry 46 and selected electrodes 26 in order to selectively sense a voltage induced in lead 20, lead extension 18, and/or electrodes 26 e.g., by RF fields generated by an MRI scanner. In some examples, based on the voltage sensed by sensing circuitry 46 over a period of time, processing circuitry 42 may calculate a root mean square (RMS) value of the sensed induced voltage (Vrms) or another metric value that may be used to quantify the induced voltage sensed by sensing circuitry 46.

Stimulation generator 44 may be a single channel or multi-channel stimulation generator. For example, stimulation generator 44 may be capable of delivering, a single stimulation pulse, multiple stimulation pulses or a continuous signal at a given time via a single electrode combination or multiple stimulation pulses at a given time via multiple electrode combinations. In some examples, however, stimulation generator 44 and switch circuitry 48 may be configured to deliver multiple channels on a time-interleaved basis. For example, switch circuitry 48 may serve to time divide the output of stimulation generator 44 across different electrode combinations at different times to deliver multiple programs or channels of stimulation energy to patient 12.

Telemetry circuitry 50 may support wireless communication between IMD 16 and an external programmer 14 or another computing device under the control of processing circuitry 42. Telemetry circuitry 50 in IMD 16, as well as telemetry modules in other devices and systems described herein, such as programmer 14, may accomplish communication by radiofrequency (RF) communication techniques. In addition, telemetry circuitry 50 may communicate with external programmer 14 via proximal inductive interaction of IMD 16 with programmer 14. Accordingly, telemetry circuitry 50 may send information to external programmer 14 on a continuous basis, at periodic intervals, or upon request from IMD 16 or programmer 14.

In some examples, telemetry circuitry 50 may support wireless communication between IMD 16 and an MRI system under the control of processing circuitry 42, either directly or indirectly (e.g., via an intermediate device such as programmer 14). For example, using telemetry circuitry 50, processing circuitry 42 may transmit information regarding the voltage induced by an RF field of an MRI scanner, e.g., during an MRI scan, and sensed via sensing circuitry 46. In some examples, IMD 16 may transmit raw or processed signal information (e.g., the determined Vrms of the sensed induced voltage) to the MRI system directly or indirectly. Based on the received information from IMD 16, the MRI system may make one or more adjustments to an MRI scan performed on patient 12. Additionally, or alternatively, IMD 16 may sense the induced voltage and determine one or more adjustments to be made to an MRI scan based on the sensed induced voltage, and then transmit instructions to the MRI system with the one or more adjustments to the MRI scan for implementation by the MRI system.

Power source 52 delivers operating power to various components of IMD 16. Power source 52 may include a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

Figure 3:
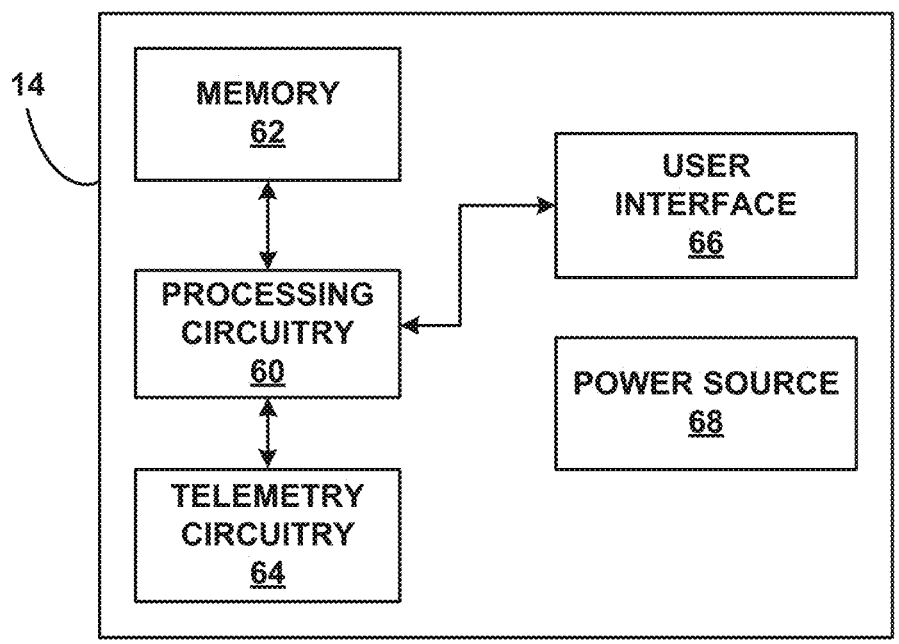
FIG. 3 is a conceptual diagram illustrating the example medical device programmer shown in FIG. 1.

FIG. 3 is a conceptual block diagram of an example external medical device programmer 14, which includes processing circuitry 60, memory 62, telemetry circuitry 64, user interface 66, and power source 68. Processing circuitry 60 controls user interface 66 and telemetry circuitry 64, and stores and retrieves information and instructions to and from memory 62. Programmer 14 may be configured for use as a clinician programmer or a patient programmer. Processing circuitry 60 may comprise any combination of one or more processors including one or more microprocessors, DSPs, ASICs, FPGAs, or other equivalent integrated or discrete logic circuitry. Accordingly, processing circuitry 60 may include any suitable structure, whether in hardware, software, firmware, or any combination thereof, to perform the functions ascribed herein to processing circuitry 60.

Memory 62 may include instructions for operating user interface 66 and telemetry circuitry 64, and for managing power source 68. Memory 62 may also store any therapy data retrieved from IMD 16 during the course of therapy. Memory 62 may include any volatile or nonvolatile memory, such as RAM, ROM, EEPROM or flash memory. Memory 62 may also include a removable memory portion that may be used to provide memory updates or increases in memory capacities. A removable memory may also allow sensitive patient data to be removed before programmer 14 is used by a different patient. Memory 62 may be considered, in some examples, a non-transitory computer-readable data storage medium comprising instructions that cause one or more processors, such as, e.g., processing circuitry 60, to implement one or more of the example techniques described in this disclosure. The term "non-transitory" may indicate that the data storage medium is not embodied in a carrier wave or a propagated signal. However, the term "non-transitory" should not be interpreted to mean that memory 62 is non-movable. As one example, memory 62 may be removed from programmer 14, and moved to another device. In certain examples, a non-transitory storage medium may store data that can, over time, change (e.g., in RAM).

Wireless telemetry in programmer 14 may be accomplished by RF communication or proximal inductive interaction of external programmer 14 with IMD 16. This wireless communication is possible through the use of telemetry circuitry 64. Accordingly, telemetry circuitry 64 may be similar to the telemetry circuitry contained within IMD 16. In alternative examples, programmer 14 may be capable of infrared communication or direct communication through a wired connection. In this manner, other external devices may be capable of communicating with programmer 14 without needing to establish a secure wireless connection.

Power source 68 may deliver operating power to the components of programmer 14. Power source 68 may include a battery and a power generation circuit to produce the operating power. In some examples, the battery may be rechargeable to allow extended operation.

In some examples, programmer 14 may be configured to communicate with both IMD 16 and an MRI system. In some examples, programmer 14 may receive information via wireless telemetry from IMD 16 regarding an induced voltage sensed by IMD 16, e.g., as a result of an RF field generated by an MRI scanner of the MRI system. Programmer 14 may then communicate the information to the MRI system, which may make one or more adjustments to an MRI scan based on the received information from programmer 14. In some examples, processing circuitry 60 of programmer 14 may determine one or more adjustments to be made to an MRI scan based on the induced voltage by IMD 16, and then transmits instructions to the MRI system with the one or more adjustments to the MRI scan for implementation by the MRI systems described herein.

Figure 4:
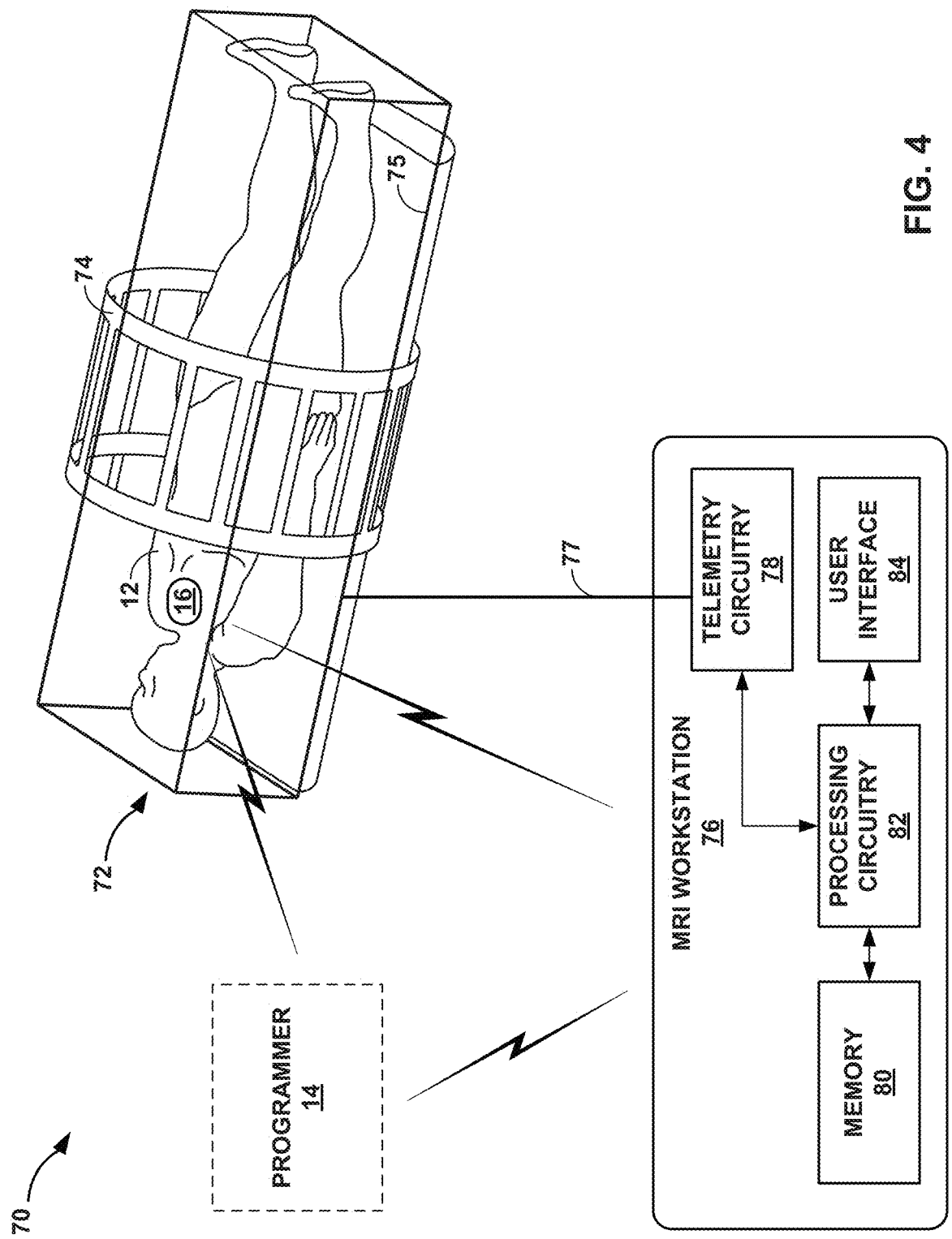
FIG. 4 is a conceptual diagram illustrating an example medical device system including an MRI scanner and workstation.

FIG. 4 is a conceptual diagram illustrating an example system 70 configured to perform an MRI scan on patient 12 in accordance with some examples of the disclosure. System 70 includes MRI scanner 72 and MRI workstation 76, which may control the operation of MRI scanner 72 during an MRI scan. MRI scanner 72 includes table 75 and MRI RF transmit coil(s) 74. MRI RF transmit coil(s) may be integrated inside the MRI bore in some examples. Additionally, or alternatively, detachable and/or local transmit coils may also be used for RF transmission during MRI. Any suitable type of MRI RF transmission configuration may be used.

As shown, during an MRI scan, patient 12 may be located on table 75 with at least a portion of patient 12 within RF transmit coil 74. MRI workstation 76 includes telemetry circuitry 78, memory 80, processing circuitry 82, and user interface 84. MRI scanner 72 and MRI workstation 76 may function together or individually as an example MRI device configured to perform an MRI scan on patient 12 with an RF field that induced a voltage in lead 20 of IMD 16.

Although not shown, MRI scanner 72 may include, e.g., a magnet, one or more RF coils, and three gradient coils. The magnet of scanner 72 generates a constant magnetic field ($B_0$) by passing current through coils within the magnet. The generated magnetic field may range from, e.g., approximately 0.5 Tesla (T) to approximately 7 T, and may align protons within the body of patient 12 either parallel or anti-parallel to the magnetic field. In some examples, MRI scanner 72 may function as a 1.5 T, 3 T, or 7 T MRI scanner.

The gradient coils may be located within the main magnet. Each gradient coil may produce three different magnetic fields that are each less strong than the main field. The gradient coils create a variable field (e.g., x, y, and z) that can be increased or decreased to allow specific and different parts of the body to be scanned by altering and adjusting the main magnetic field. The RF coil(s) may transmit RF pulses or wave into patient 12, which excite protons from parallel to anti-parallel alignment. In response to the force bringing the protons back to their equilibrium orientation, the protons undergo a rotating motion (precession) and return to parallel alignment. This appears as a magnetic flux, which yields a changing voltage in one or more receiver coils or antennas (not shown) of scanner 72 to produce an MRI output signal.

In some examples, the RF pulses or wave transmitted by the RF coil(s) may have a frequency of approximately 1 MHz to approximately 1 GHz. MRI RF resonance frequency scale linearly with field strength, e.g., the frequency may be about 64 MHz at 1.5 T and 128 MHz at 3.0 T. These example frequencies may be for imaging hydrogen. In some examples, evaluation of implantable medical devices is performed at 1.5 T and 3 T (64 and 128 MHz) for MRI labeling of the implantable medical devices because the two may constitute about 90% of clinical MRI scans, but other frequencies can also be evaluated. Different nuclei (e.g., example sodium, phosphorus, and the like) have different resonance frequencies, and these frequencies are generally lower than hydrogen. In some examples, a 10.5 T magnetic field MRI scanner may operate at 450 MHz.

MRI workstation 76 may receive the output signal from scanner 72 via telemetry circuitry 78 and generate an image based on the output signal that is graphically displayed to a user via user interface 84. MRI workstation 76 and MRI scanner 72 may be in different rooms separated by a wall. MRI workstation 76 may be in electrical communication with MRI scanner 72 via control and communication line 77.

Processing circuitry 82 controls operation of scanner 72, user interface 84 and telemetry circuitry 78, and stores and retrieves information and instructions to and from memory 80. In some examples, processing circuitry 82 may control one or more parameters related to the RF excitation of the MRI scan carried out by the MRI system that may be adjusted, e.g., to adjusted to provide for different electric field distribution from the MRI scan. Examples parameters may include RF shimming settings (e.g., the relative magnitude and phase of the transmit signal in different channels of multi-transmit systems), RF transmit pulse waveforms applied to different transmit channels, RF pulse duration (e.g., the length of the RF pulse), RF pulse repetition period, and RF pulse waveform shape. Modifications to the RF shimming settings and/or RF transmit pulse waveforms applied to different transmit channels may change the electric and magnetic field distribution from the MRI scan inside patient 12. RF pulse duration (e.g., the length of the RF pulse), RF pulse repetition period, and/or RF pulse waveform shape may be modified by processing circuitry 82 to alter the amount of power applied by the MRI scanner 72, which may be tailored to reduce total RF heating, e.g., of lead 18 within patient 12.

Processing circuitry 60 may comprise any combination of one or more processors including one or more microprocessors, DSPs, ASICs, FPGAs, or other equivalent integrated or discrete logic circuitry. Accordingly, processing circuitry 82 may include any suitable structure, whether in hardware, software, firmware, or any combination thereof, to perform the functions ascribed herein to processing circuitry 82.

Memory 80 may include instructions for operating scanner 72, user interface 84 and telemetry circuitry 78. Memory 80 may also store any data retrieved from IMD 16 including information regarding sensed voltage induced in IMD 16 by scanner 72. Memory 80 may include any volatile or non-volatile memory, such as RAM, ROM, EEPROM or flash memory. Memory 80 may also include a removable memory portion that may be used to provide memory updates or increases in memory capacities. Memory 80 may be considered, in some examples, a non-transitory computer-readable data storage medium comprising instructions that cause one or more processors, such as, e.g., processing circuitry 82, to implement one or more of the example techniques described in this disclosure. The term "non-transitory" may indicate that the storage medium is not embodied in a carrier wave or a propagated signal. However, the term "non-transitory" should not be interpreted to mean that memory 80 is non-movable. As one example, memory 80 may be removed from workstation 76, and moved to another device. In certain examples, a non-transitory storage medium may store data that can, over time, change (e.g., in RAM).

Telemetry circuitry 78 supports communication between MRI scanner 72 and workstation 76, e.g., via communication line 77. The communication between MRI scanner 72 and workstation 76 may allow for scanner 72 to be operated under the control of workstation 76. The MRI settings which define the operation of scanner 72 may be entered, e.g., via user interface 78 of workstation 76 by an operator of system 70.

Telemetry circuitry 78 may also support communication (e.g., wireless communication) between IMD 16, external programmer 14 or another computing device, and workstation 76 under the control of processing circuitry 82. Telemetry circuitry 78 in workstation 76, as well as telemetry modules in other devices and systems described herein, such as programmer 14 and IMD 16, may accomplish communication by radiofrequency (RF) communication techniques or other suitable techniques. In addition, telemetry circuitry 78 may communicate with external programmer 14 via proximal inductive interaction of IMD 16 with programmer 14. Accordingly, telemetry circuitry 50 may send information to external programmer 14 on a continuous basis, at periodic intervals, or upon request from IMD 16 or programmer 14.

In some examples, telemetry circuitry 78 may support wireless communication between IMD 16 and workstation 76 under the control of processing circuitry 82, either directly or indirectly (e.g., via an intermediate device such as programmer 14). For example, using telemetry circuitry 78, processing circuitry 82 may receive information from IMD 16 regarding the voltage induced by an RF field of MRI scanner 72, e.g., during an MRI scan, and sensed via sensing circuitry 46 of IMD 16. In some examples, processing circuitry 82 may receive raw or processed sensed voltage information (e.g., the determined Vrms of the sensed induced voltage) from IMD 16 directly or indirectly. Based on the received information from IMD 16, processing circuitry 82 may make one or more adjustments to an MRI scan performed on patient 12 by MRI scanner 72. Additionally, or alternatively, processing circuitry 82 may receive one or more adjustments to be made to an MRI scan from IMD 16 and/or programmer 14. IMD 16 and/or programmer 14 may determine the adjustments based on the induced voltage sensed by IMD 16, and then transmit instructions to processing circuitry 82 with the one or more adjustments to the MRI scan for implementation by MRI scanner 72.

In some examples, MRI scanner 72 may be configured to modify the magnetic field distribution and electric field distribution of an MRI scan. Electric and magnetic field distributions inside patient 12 may depend, e.g., on the RF coil design, excitation method (e.g. circularly-polarized, linearly-polarized, or arbitrary excitation), position of the subject inside the MRI scanner, subject physical properties and/or the like.

The rotating component of the magnetic field distribution may be the desired component of the excitation field, and this field component tilts proton spins away from the equilibrium thereby generates the MRI signal. It may be preferred that this magnetic field distribution is relatively uniform inside the imaging region of interest in patient 12. Electric field may be the unwanted component of the excitation during an MRI scan but it may not possible to get rid of it due to the physics of an MRI scan. At some MRI frequencies, to be able to generate a desired magnetic field, there may be some residual electric field that cannot be avoid. The electric field is not useful to the performance of an MRI scan, and it contributes to heating during an MRI scan(local heating of the tissue, as well as coupling to IMD and RF lead heating).

At 1.5 T (e.g. 64 MHz), example quadrature MRI transmit coil designs are capable of providing uniform magnetic field distributions. However, at 3 T (e.g. 128 MHz), depending on the size of the patient being imaged (e.g. high BMI patients, torso/pelvis scans etc), some example quadrature MRI transmit coil designs may not be able to produce a uniform magnetic field distribution inside the imaging region-of-interest. Therefore, in some example, MRI systems may employ multi-channel transmit coils and shimming strategies to tailor the magnetic field distribution inside the patient and to achieve uniform excitation at 3 T (although multi-channel transmit systems may be used at lower fields strengths (e.g., 1.5 T or less).

Figure 5:
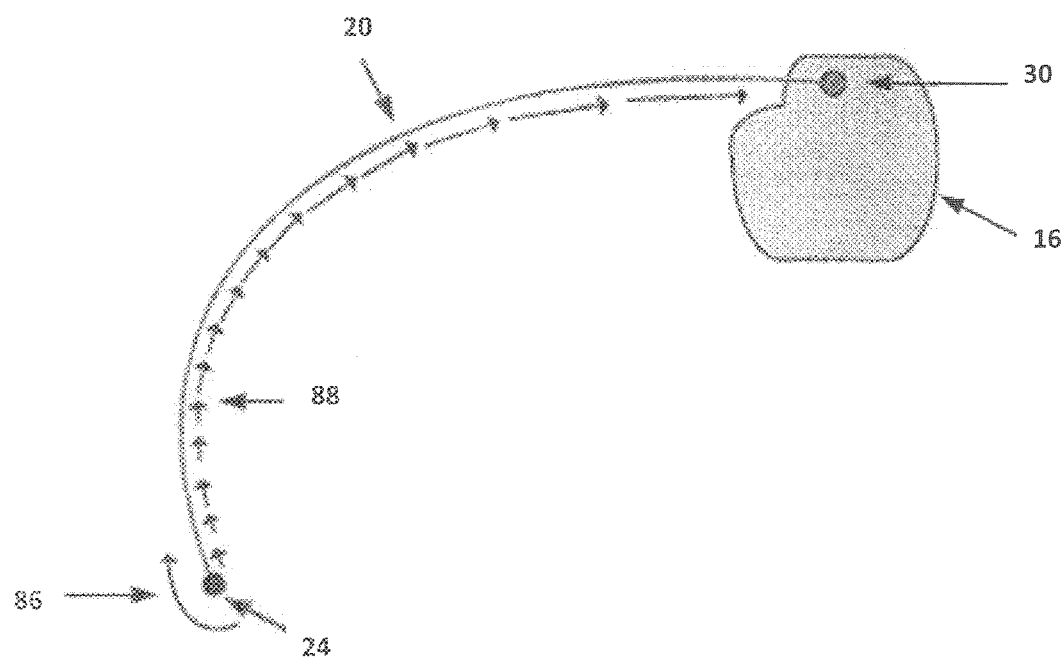
FIG. 5 is a conceptual diagram illustrating an example voltage induced in an IMD by an RF field generated by an MRI scanner.

FIG. 5 is a conceptual diagram illustrating IMD 16 of system 10 including lead 20 and electrode(s) 26 during an MRI scan. The MRI scan may be performed by MRI scanner 72 (not shown). During the MRI scan, one or more RF transmitter coils of MRI scanner 72 may generate RF waves or pulses which induces RF electric field 88. RF electrical field 88 induces a voltage within lead 20, which results in heating (e.g., an increase in temperature) of electrode 26. The heating of electrode(s) 26 may result in the heating of tissue 86 of patient 12 adjacent to electrode(s) 26. To prevent undesired damage to tissue 86 of patient 12, it may be desirable to reduce or otherwise limit the heating to electrode(s) resulting from RF electric 88 during an MRI scan. For example, it may be desirable to prevent the temperature of electrode(s) 26 from increasing above, e.g., approximately 2 degrees Celsius, or some other temperature threshold during an MRI scan.

Examples of the disclosure may allow for a system such as system 70 to predict the level of RF heating (e.g., in terms of temperature increase of electrode(s) 26 over a period of time and/or rate of temperature increase) to identify MRI scan settings that provide for a desired heating of tissue 86 during an MRI scan (e.g., by identifying MRI settings that result in a temperature increase of electrode(s) 26 that is at or below a threshold value). As described herein, this prediction may be based on the voltage induced by the RF field of an MRI scanner on conductive lead 20 that is sensed by IMD 16. Such a technique may employ the sensed induced voltage as a marker of RF heating of electrode(s) 26 and may be used prior to performing an actual MRI scan on the patient that results in an image that is viewable by a user.

Additionally, or alternatively, examples of the disclosure may also allow for a system such as system 70 to estimate the heating of electrode(s) 26 during an actual MRI scan. The temperature estimation may be based on the voltage induced by the RF field of an MRI scanner on conductive lead 20 that is sensed by IMD 16. In some examples, based on the estimated temperature of electrode(s) 26 while an MRI scan is being performed, one or more settings of the MRI scan may be adjusted, e.g., to prevent heating of tissue 86 from increasing above a threshold level. In some examples, the adjustments may include adjusting the power of the RF pulses (or waves), adjusting the shimming setting of the RF pulses (or wave(s)), and/or adjusting the duration of the MRI scan based on the sensed induced voltage.

Figure 6:
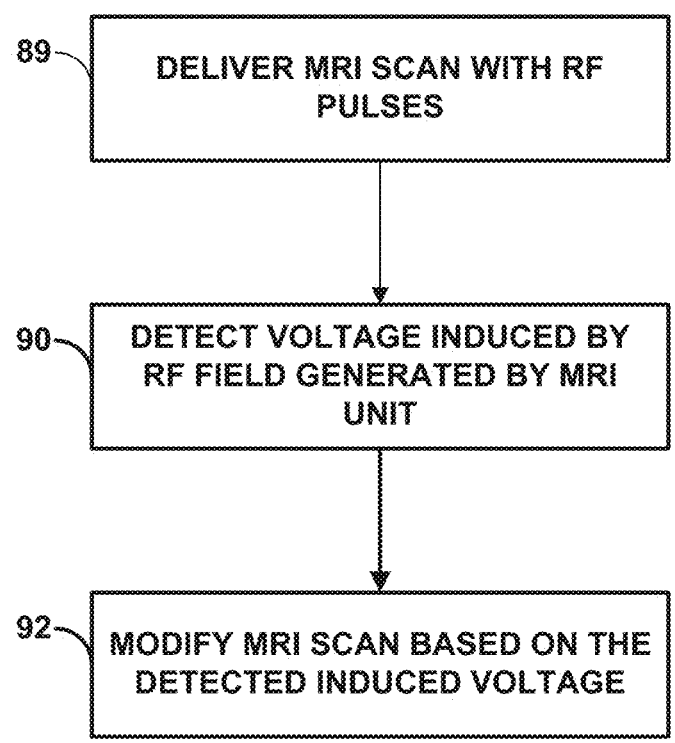
FIG. 6 is a flow diagram illustrating an example technique in accordance with some examples of the disclosure.

FIG. 6 is a flow diagram illustrating an example technique for modifying an MRI scan based on a voltage induced in lead 20 by RF fields generated by RF coil(s) of MRI scanner 72. For ease of description, the example technique of FIG. 6 is described with regard to system 70 shown in FIG. 4. However, any suitable system including an IMD configured to sense voltage induced in a portion of the IMD (e.g., one or more conductive leads) during an MRI scan may be employed to perform the example technique of FIG. 6.

As shown in FIG. 6, processing circuitry 82 may control MRI scanner 72 to deliver an MRI scan with RF pulses that generates an RF field within patient 12 (89). The RF field may be generated by the delivery of a plurality of RF pulses (or RF waves) by one or more RF coils of MRI scanner 72 in the presence of a constant magnetic field ($B_0$). In some examples, the MRI scan delivered by MRI scanner 72 may be used during an actual MRI scan that generates an MRI of one or more anatomical locations of patient 12. In other examples, the MRI scan delivered by MRI scanner 72 may be used only as a test scan (e.g., with relatively low power and small number of RF pulses) so that the voltage induced by the RF field may be detected and evaluated for possible changes prior to performing an actual MRI scan on patient 12 that generates an MRI of one or more anatomical locations of patient 12.

System 70 may then detect the voltage induced in lead 20 by the RF field generated by the MRI device (90). For example, to detect the induced voltage, IMD 16, under the control of processing circuitry 42, may sense the voltage induced in lead 20 by the generated RF field using sensing circuitry 46 (90). Any suitable sensing vector may be used by sensing circuitry 46 to sense the induced voltage. The sensing vector may employ at least one of electrodes 26 on lead 20 in a unipolar (e.g., using the housing of IMD 16 as one of the sense electrodes), bipolar, or multipolar configuration. Processing circuitry 42 may analyze the sensed voltage signal to determine the Vrms of the induced voltage in lead 20. For ease of description, examples of the disclosure are primarily described as using Vrms as a metric to quantify the sensed induced voltage although other metrics may be employed in addition to, or as an alternative, to Vrms.

In some examples, IMD 16, under the control of processing circuitry 42, may sense the voltage induced in lead 20 by measuring the voltage between an electrode wire or other conductor within lead 20 electrically coupled to electrode 26 and the common ground (e.g. case, can or housing of IMD 16). Any electrode wire or other conductor within lead 16 may be used. The detected voltage may be the voltage measured after a filtered feed through capacitor between the proximal end of the electrode wire in lead 20 and a common ground (such as the case enclosure, can or housing of IMD 16). In some examples, IMD 16, under the control of processing circuitry 42, may sense the voltage between different electrode wires or other conductors of coupled to respective electrodes 26 of lead 20.

Upon sensing the induced voltage, to allow MRI workstation 76 to detect the induced voltage, IMD 16 may transmit a signal to MRI workstation 76 indicating that a voltage in lead 20 has been sensed as result of the RF field generated by MRI scanner 72. In some examples, IMD 16 may transmit information to MRI workstation 76 that indicates the Vrms determined for the sensed induced voltage. In other examples, IMD 16 may transmit the raw or processed sensed voltage signal to MRI workstation 76, and then processing circuitry 82 of MRI workstation 76 may determine the Vrms of the induced voltage based on the received signal information.

System 70 may then modify, based on the detected induced voltage, one or more parameters of the MRI scan that was delivered to induce the voltage in lead 20 that was sensed by IMD 16 (92). In some examples, system 70 may estimate the temperature of electrode(s) 26 based on the detected induced voltage during an actual MRI scan. In such examples, the modification may include one or more adjustments to the MRI scan being performed by MRI scanner 72 based on the estimated temperature, such as ending the MRI scan, continuing the MRI scan, adjusting the power of the RF field, adjusting the shimming setting of the MRI scan, adjusting the anatomical location of the MRI scan, or some combination thereof. In some examples, the modification to the MRI scan may be configured to reduce or stop the heating of electrode(s) 26 resulting from the MRI scan being performed when the induced voltage in lead 20 was detected. In some examples, such modification may also result in reducing the level of the voltage induced by the RF field of the MRI scan.

Additionally, or alternatively, the same or similar process may be made prior to performing an actual MRI scan, e.g., by delivering a test MRI scan from MRI scanner 72, detecting the voltage induced by the RF field of the delivered test MRI scan, and modifying the MRI scan in the manner described above based on the detected induced voltage. In such an example, the modification to the test MRI scan may be configured to result in a desired level of heating of electrode(s) 26 during an actual MRI scan performed on patient 12 using the modified MRI scan parameters determined by the described process in advance of the actual MRI scan.

The modifications to the MRI scan based on the detected induced voltage (92) may be determined by one or a combination of processing circuitry 42, 60, and 82. MRI scanner 72 may implement the determined modifications under the control of one or a combination of processing circuitry 42, 60, and 82. Any suitable communication arrangement may be used between IMD 16, programmer 14, and the MRI system (e.g., MRI workstation 76 and/or MRI scanner 72). IMD 16 may communicate directly with MRI workstation 76 and/or MRI scanner 72 via telemetry circuitry 50 and telemetry circuitry 78. In other examples, IMD 16 may communicate indirectly with MRI workstation 76 and/or MRI scanner 72 by way of one or more other external devices. For example, IMD 16 may communicate indirectly with MRI workstation 76 and/or MRI scanner 72 through programmer 14 using telemetry circuitry 50, telemetry circuitry 64, and telemetry circuitry 78. In some examples, MRI workstation 76 may communicate information received from IMD 16 to MRI scanner 72 via communication line 77. In some examples, IMD 16 may additionally or alternatively communicate directly with MRI scanner 72 or indirectly through programmer 14.

In one example, the wireless telemetry used by system 70 may use a wireless communication frequency and emissions are outside of the MRI frequency used by MRI scanner 72. For example, system 70 may use 450 MHz telemetry or 2.4 GHz Bluetooth telemetry as long as there are no emissions in the MRI frequency band. Alternatively, system 70 may be configured to use wireless telemetry while signals are not being transmitted and/or received by the MRI system to avoid potential interference.

In one example, a master-servant approach may be used in which MRI workstation 76 and/or MRI scanner 72 is the master and IMD 16 is the servant. The processing and MRI adjustments may be performed by MRI workstation 76 and/or MRI scanner 72, with IMD 16 sensing the induced voltage in lead 20 and reporting the induced voltage value(s) (e.g., in terms of determined Vrms) to MRI workstation 76 and/or MRI scanner 72.

In another example, a master-servant approach may be used in which MRI workstation 76 and/or MRI scanner 72 is the servant and IMD 16 is the master. In such an example, processing circuitry 42 of IMD 16 determines the adjustments to an MRI scan based on the sensed inducted voltage and then controls MRI scanner to deliver an MRI scan according to the adjusted MRI settings (e.g., according to a selected shimming setting).

In another example, communication between IMD 16 and MRI workstation and/or MRI scanner 72 is accomplished using a third device, such as programmer 14. In such an example, MRI workstation 76 and/or MRI scanner 72 and IMD 16 do not directly establish communications, but instead use a third device. In some examples, the third device acts as the master, where IMD 16 senses and reports induced voltage values to the third device. Similarly, MRI workstation 76 and/or MRI scanner 72 reports the MRI settings for the MRI scan that induced the sensed voltage (e.g., in term of shim settings used) to the third device. The third device then determines any modifications to the MRI settings (e.g., modifications to the shimming setting) based on the reported voltage values and then dictates the modification to MRI workstation 76 and/or MRI scanner 72.

Figure 7:
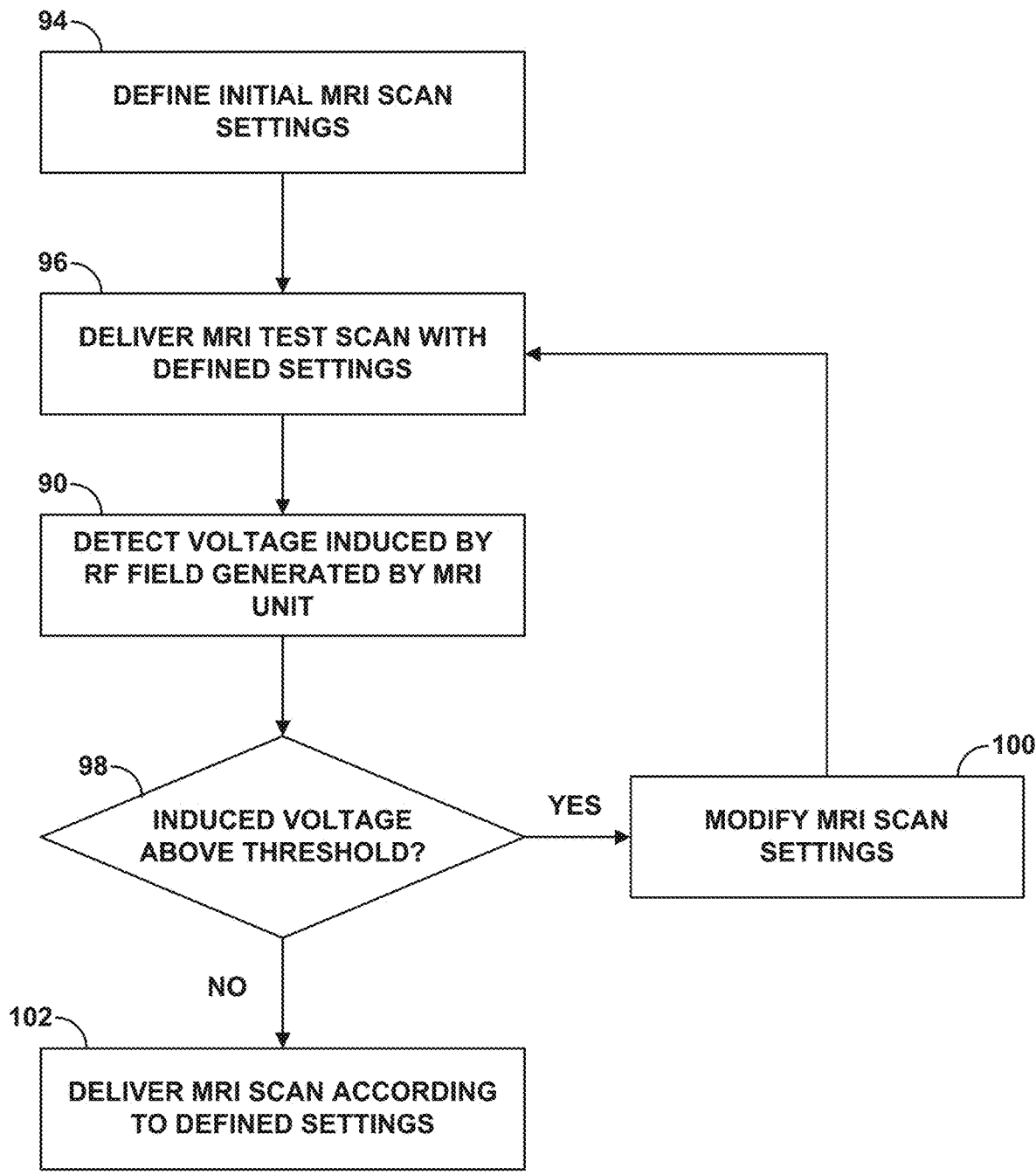
FIG. 7 is a flow diagram illustrating another example technique in accordance with some examples of the disclosure.

FIG. 7 is a flow diagram illustrating an example technique that may be employed by a system such as system 70 to modify one or more MRI setting based on a sensed voltage in lead 20. For ease of description, the example technique of FIG. 7 is described with regard to system 70 shown in FIG. 4. However, any suitable system including an IMD configured to sense voltage induced in a portion of the IMD (e.g., one or more conductive leads) during an MRI scan may be employed to perform the example technique of FIG. 7.

As shown in FIG. 7, processing circuitry 82 of MRI workstation 76 may define an initial set of values for MRI scan settings (94), and MRI scanner 72 may deliver a test scan to patient 12 according to the defined initial MRI settings (96). The initial MRI scan settings (e.g., default settings set by a manufacturer, clinician or other machine user) may include values for one or more parameters to be used by MRI scanner 72 to deliver a test scan to patient 12. The MRI settings may include the power of the generated by MRI scanner 72, shimming settings for the RF field generated by the one or more coils of MRI scanner 72, and other settings including those settings that may influence the level of voltage induced in lead 20 by the RF field of the delivered MRI test scan (96). Shimming settings may refer to the relative magnitude and phase of different channels of the RF transmit coils of MRI scanner 72. The test scan may be different from an actual MRI scan that is used to generate one or more MRI images of an anatomical location of patient 12. For example, the delivered MRI test scan may not be used to generate an MRI image of patient 12 but instead may be used to test the voltage induced by the RF field generated by scanner 72 when the MRI scan is delivered in accordance with the defined initial MRI settings.

In some example, the MRI test scan may be performed at relatively low power and with a relatively low number of RF pulses, e.g., to prevent undesired heating of electrode 26 during the test scan. The test scan may be long enough so that an accurate sensing of induced voltage can be performed, e.g., about millisecond, or about 0.5 milliseconds to about 10 milliseconds, or about a millisecond to about 10 milliseconds. Also, the pulses may be transmitted as frequent as the IMD can recover and perform new sensed voltage readings again (e.g., about 50 pulses per second), which may be hardware/firmware and system implementation dependent.

IMD 16, using processing circuitry 42 and sensing circuitry 46, may detect a voltage induced in lead 20 by the RF field generated by MRI scanner 72 during the test scan (90). For example, IMD 16 may sense multiple voltage values over a sensing period and then determine the Vrms for the induced voltage using the multiple sample values. IMD 16 may then transmit the determined Vrms value to MRI workstation 76 and/or MRI scanner 72. MRI workstation 76 and/or MRI scanner 72 may then determine whether or not the induced voltage, e.g., the Vrms value determined by IMD 16, is above a threshold value (98). The threshold value may be a value for the induced voltage that has been determined to correspond to the maximum voltage that may be induced by an RF field during an MRI scan over a set period of time that does not result in electrode(s) 26 increasing in temperature beyond a maximum desired temperature. Such a threshold value may be MRI frequency, IMD 16 (e.g. filtered feed through capacitor value), design of lead 20, and implant location dependent, and may need to be evaluated and set for different IMD 16 and lead 20 designs. Additionally, the Vrms threshold value may be different at different MRI frequencies (e.g., the threshold value may be different for 64 MHz and 128 MHz).

If the determined Vrms value for the detected induced voltage in lead 20 is less than or equal to the threshold value (98), the MRI scanner 72 may then deliver an actual MRI scan to patient 12 according to the defined MRI settings (102). Conversely, if the determined Vrms value for the detected induced voltage is greater than the threshold (98), then MRI workstation 76 and/or MRI scanner 72 may modify the MRI scan settings (100), i.e., make one or more adjustments to the initial MRI scan settings. The adjustments to the MRI scan settings may be designed to reduce the level of voltage induced by the RF field generated by MRI scanner 72.

As one example, the shimming settings (e.g., relative magnitude and phase of the RF pulses or RF waves) may be adjusted to create a different electric field during the MRI scan that may reduce the voltage induced in lead 20. The adjustment to the shimming setting may include a change in the relative magnitude (increase or decrease) of one or more coils and/or phase (increase or decrease) of one or more coils. The changes to shimming setting may be made to one channel or multiple channels of MRI scanner 72. The adjustment to the shimming setting may result in the induced voltage to increase, decrease, or stay substantially the same. In one example, sensing circuitry 46 may be configured to measure the phase of the induced voltage, then sense the induced voltage due to two different shimming settings to be able to determine what a desirable shimming setting would be, e.g., a setting that results in an induced voltage less than or equal to the threshold value.

In some examples, MRI workstation 76 and/or MRI scanner 72 may modify the MRI scan settings to adjust the induced voltage by modifying the relative magnitude and phase of different transmit channels, modifying the RF pulse waveform, modifying RF pulse waveform of different transmit channels, modifying the pulse duration, and/or modifying the pulse repetition time. Using the technique of FIG. 7, the modifications to the shimming setting and/or other MRI scan setting(s) may continue until the induced voltage (measured as Vrms) in lead 20 is less than or equal to the threshold value (98). The changing the electric field resulting from the changing MRI settings may affect the magnetic field distribution. For example, some low electric field coupling shimming settings may not be desirable for imaging. However, as long as sufficient magnetic field uniformity as achieved inside the imaging region-of-interest, clinically suitable imaging may be performed and those MRI setting may be utilized for an MRI scan on patient 12.

While the technique of FIG. 7 describes a process for identifying an MRI setting that results in a voltage induced by the RF field generated by MRI scanner 72 below a threshold value, the process may be modified to identify MRI settings that result in the lowest induced voltage from a plurality of different MRI settings. In such an example, each MRI setting may be tested by delivering a test MRI scan according to the MRI setting (96) and the voltage induced by the RF field generated according to the MRI settings may be detected. In some examples, each different MRI setting may have a different shimming setting. After each different MRI setting is tested, processing circuitry 82, for example, may identify the particular MRI setting that resulted in the lowest induced voltage and then deliver an actual full MRI scan using the identified MRI settings.

In some examples, MRI workstation 76 and/or MRI scanner 72 and IMD 16 can establish one-way or two-way communications (e.g., using Bluetooth or a different frequency band). MRI workstation 76 and/or MRI scanner 72 may output a variety of different RF shimming settings, while IMD 16 records the induced voltage for each shimming setting. In a closed loop system, an algorithm may be used by processing circuitry 42, 60, and/or 82 to select the MRI shimming setting that allows for the least amount of RF heating or maintains the temperature of electrode(s) 26 below a threshold temperature. In some examples, the algorithm run by processing circuitry 42, 60, and/or 82 may be designed to select the shimming setting that yields minimum Vrms or a shimming setting that yields Vrms less than a "safe" threshold, e.g., a threshold that corresponds to electrode(s) 26 remaining below a desired temperature during the MRI scan.

While the example technique of FIG. 7 is described as being used prior to delivering a full MRI scan according to MRI settings identified using the example process, such a technique may be used additionally or alternatively during an actual MRI process. For example, MRI scanner 72 may initiate the delivery of an actual MRI scan that is configured to generate an MRI image. At some point during the MRI scan, IMD 16 may detect the voltage induced by the RF field generated by MRI scanner 72 during the MRI scan that is being carried out. IMD 16 may determine the Vrms of the induced voltage based on the sensed voltage and determine whether or not the determined Vrms is greater than a threshold value. If not, MRI scanner 72 may continue the MRI scan without modifying the MRI scan settings and IMD 16 may continue to monitor the Vrms of the induced voltage. Conversely, if the Vrms determined for the sensed induced voltage is greater than the threshold value, MRI scanner 72 and/or MRI workstation may modify the MRI settings. As described above, the modification to the MRI settings may be configured to reduce the level of voltage induced on lead 20 by the generated RF field of the scan. Such a process may be used continuously during an MRI scan in a manner that maintains electrode(s) 26 below a threshold temperature.

Figure 8:
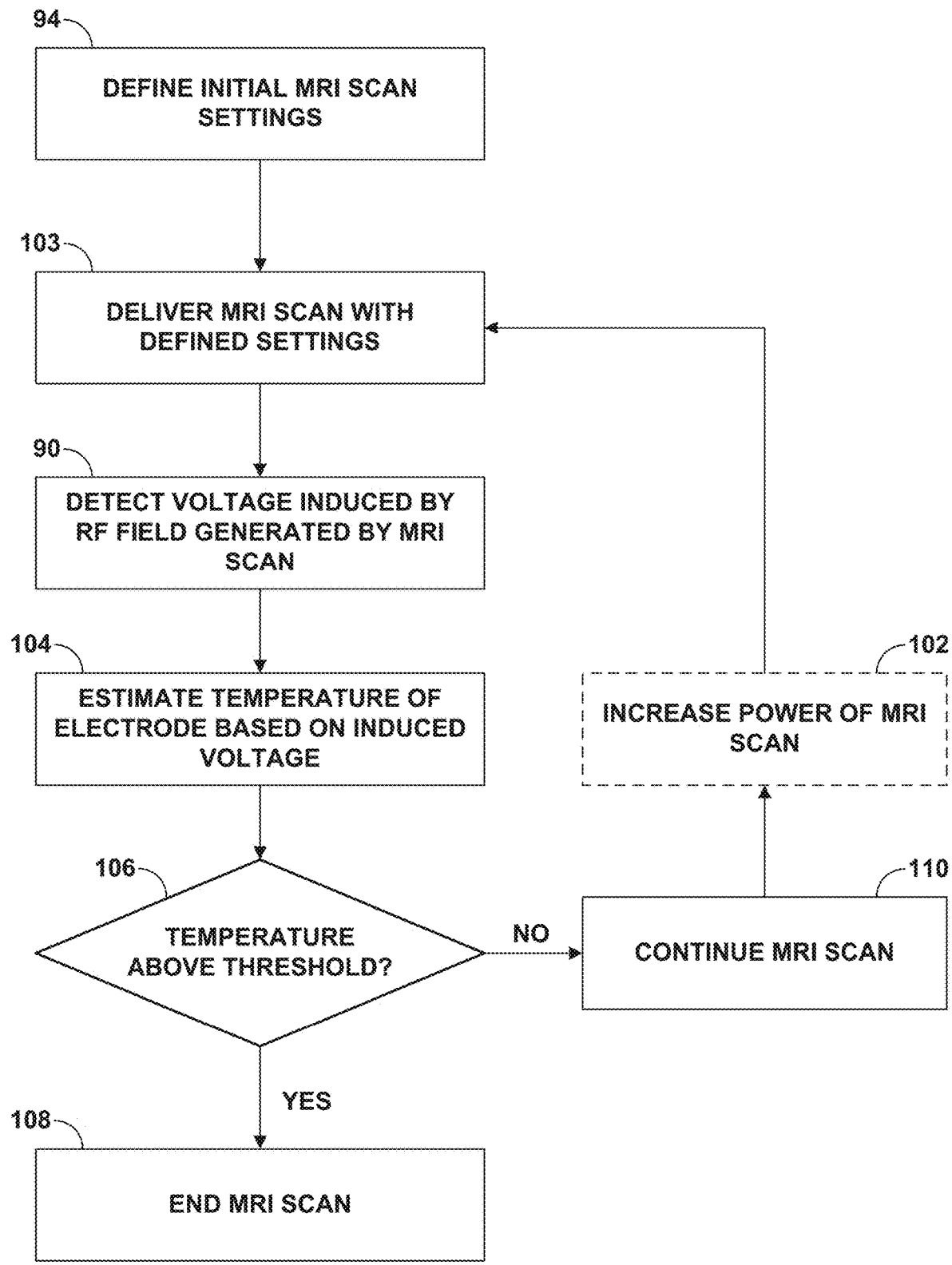
FIG. 8 is a flow diagram illustrating another example technique in accordance with some examples of the disclosure.

FIG. 8 is another example technique that may be used to control the temperature of electrode(s) 26 on lead 20 of IMD 16 during an MRI scan. The example technique of FIG. 8 may be used in combination with the example technique of FIG. 7 or as an alternative to the example technique of FIG. 7. Again, for ease of description, the example technique of FIG. 7 is described with regard to system 70 shown in FIG. 4. However, any suitable system including an IMD configured to sense voltage induced in a portion of the IMD (e.g., one or more conductive leads) during an MRI scan may be employed to perform the example technique of FIG. 7.

In some examples, the example technique of FIG. 8 may be employed when MRI scanner 72 is not able to modify shimming settings of an MRI scan, particularly in a manner that may reduce the level of voltage induced in lead 20. For example, MRI scanner 72 may take the form of a 1.5 T scanner without the capability of changing the excitation field of the MRI scan. In such cases, system 70 may be configured to make adjustments other than that of shimming setting adjustments during an MRI scan in order to reduce the RF heating of electrode(s) 26 or otherwise prevent electrode(s) 26 from increasing beyond a threshold temperature during a scan.

As shown in FIG. 8, processing circuitry 82 of MRI workstation 76 may define an initial set of values for MRI scan settings (94), and MRI scanner 72 may deliver an actual MRI scan to patient 12 according to the defined initial MRI settings (103). An actual MRI scan may be performed with the goal of generating an MRI of one or more anatomical locations of patient 12 rather than simply delivering the RF field and other components of the MRI scan in as a test scan as described in the example of FIG. 7.

IMD 16, using processing circuitry 42 and sensing circuitry 46, may then detect a voltage induced in lead 20 by the RF field generated by MRI scanner 72 during the MRI scan (90). For example, IMD 16 may sense multiple voltage values over a sensing period and then determine the Vrms for the induced voltage using the multiple sample values.

IMD 16 may then transmit the determined Vrms value to MRI workstation 76 and/or MRI scanner 72. In some examples, IMD 16 may sense the induced voltage using a rolling window so that the Vrms or other sensed voltage metric is continuously updated and monitored during an MRI scan, and can capture any changes in induced voltage that may occur during the scan.

Using the determined Vrms, processing circuitry 42, 60, and/or 82 may estimate the temperature of electrode(s) 26 during the scan, e.g., in approximately real-time (104). For example, processing circuitry 42, 60, and/or 82 may use one or more algorithms to estimate the temperature of electrode (s), where the one or more algorithms use Vrms (or other measure of induced voltage on lead 20) as an input, e.g., in addition to other input parameters. As will be described below in the Examples section, in some examples, input parameters used by one or more modeling algorithms for estimating the temperature of electrode(s) 26 during an MRI scan may include patient specific parameters (e.g., patient height, patient weight, position of lead within the patient, MRI scan location relative to implant), lead specific parameters (e.g. lead length, extension length) and MRI specific parameters (e.g., RF coil length, RF coil diameter) along with induced voltage.

Figure 17:
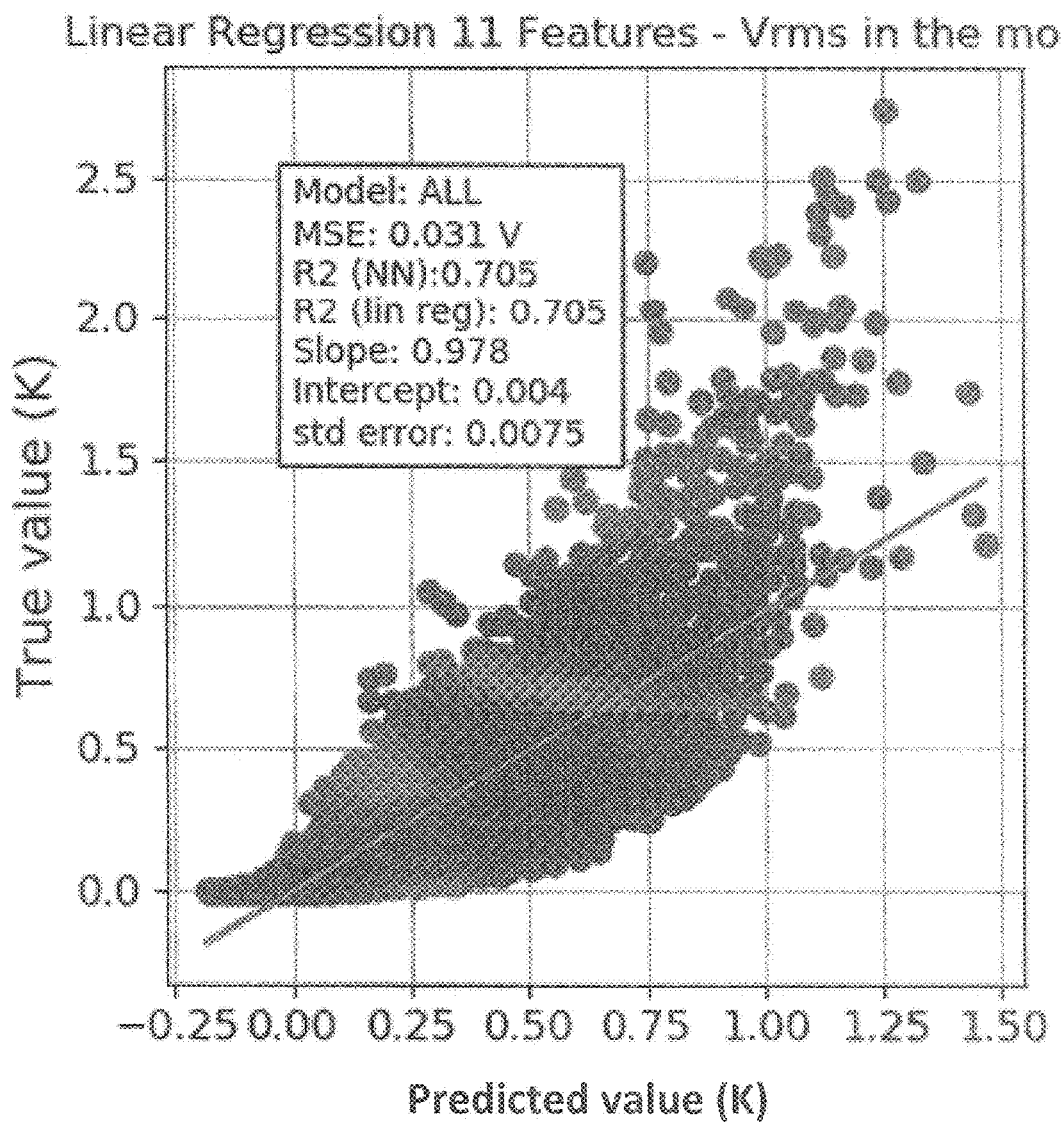
Figure 18:
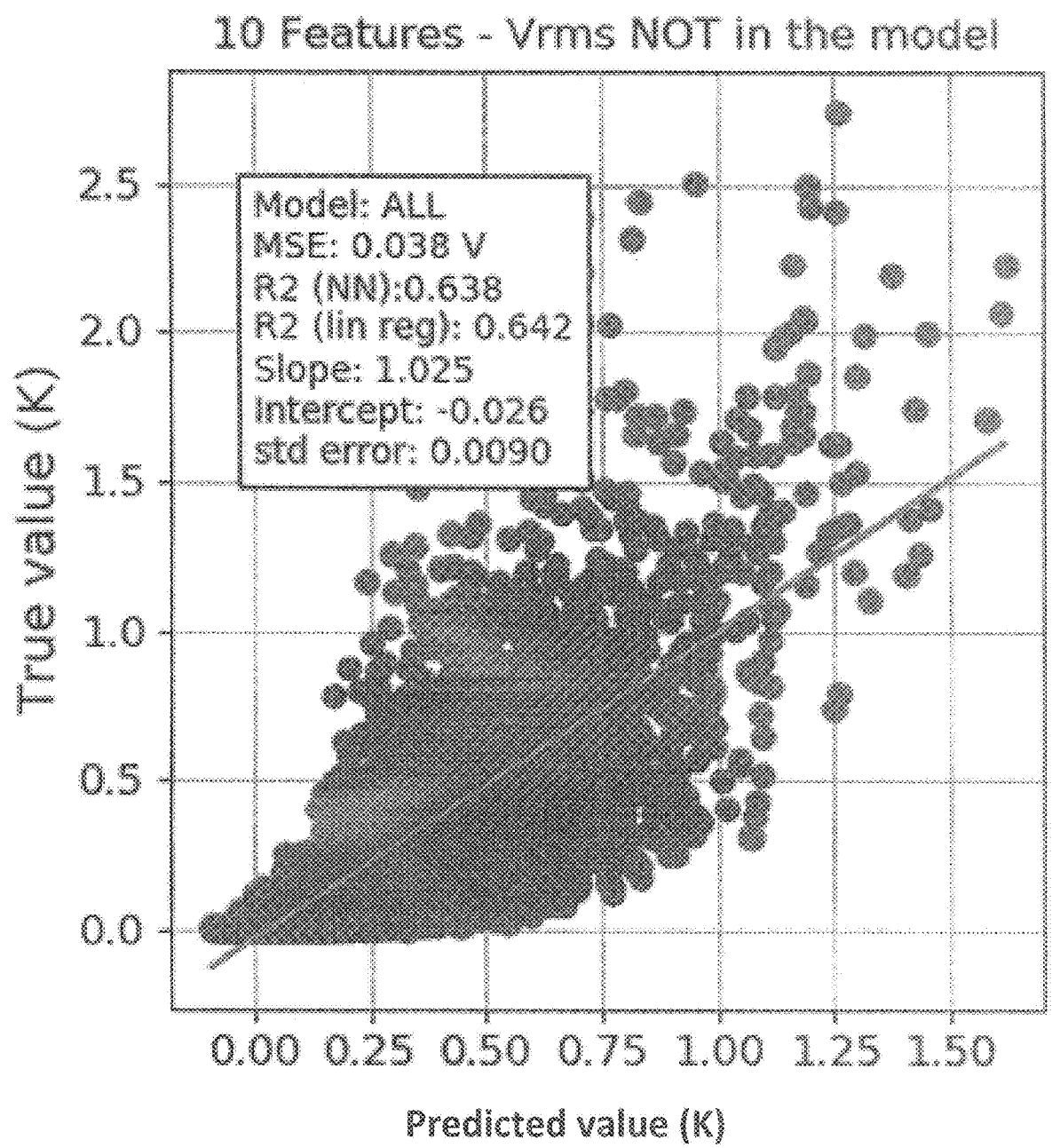
Figure 19:
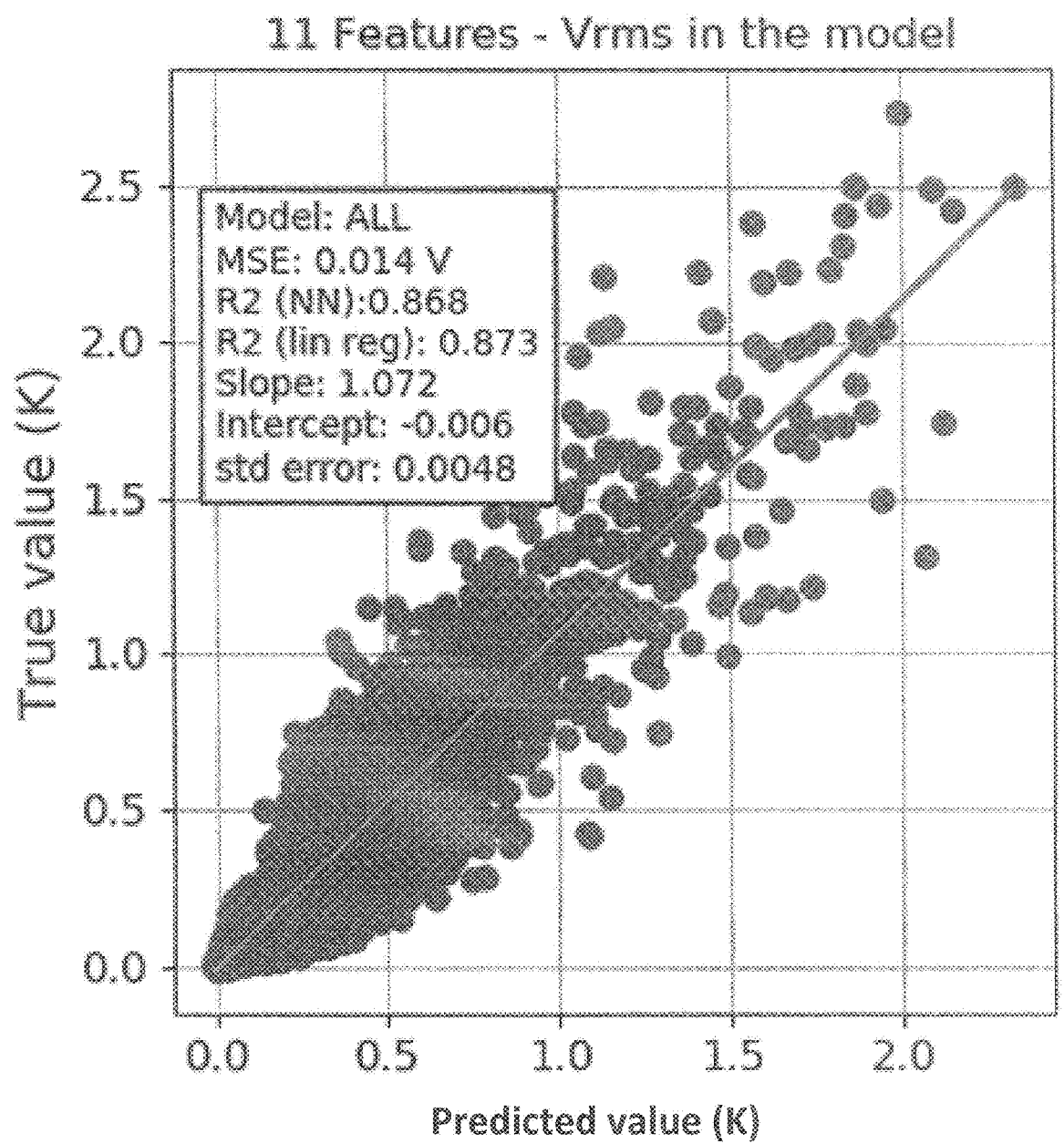

Any suitable algorithm may be used by processing circuitry 42, 60, and/or 82 to estimate the temperature of electrode(s) 26 (104) based on the detected voltage induced by the RF field generated by MRI scanner 72 during an MRI scan (103). For example, suitable algorithms may include algorithms the same or substantially similar to those described below with regard to FIGS. 16-19. As described below, FIGS. 16 and 17 relate to multiple linear regression models used to estimate the temperature of electrode(s) during an MRI scan. The model of FIG. 16 was developed without including induced voltage as an input parameter in the model. The model of FIG. 17 was the same as FIG. 16 with the only difference being induced voltage (e.g., Vrms) on the lead as an input parameter in the model. FIGS. 18 and 19 relate to artificial neural network predictive models used to estimate the temperature of electrode(s) during an MRI scan. The model of FIG. 18 did not include induced voltage (e.g., Vrms) as an input parameter while the model of FIG. 19 did include induced voltage (e.g., Vrms) as an input parameter in the predictive model. Other model features or input parameters used in the models described herein may include patient height, patient weight, patient weight, MRI scan location, lead length, lead implant location, IMD implant location, MRI RF coil length, MRI RF coil diameter, MRI quadrature excitation polarity, and/or Vrms (not used in the model of FIGS. 16 and 18). Predictive models or models for estimating the RF heating of electrode(s) 26 during an MRI scan may be developed using linear regression, support vector machine, decision tree, artificial neural networks, other predictive algorithms or a combination of two or more of these algorithms, and using induced voltage as a feature in the predictive or other type model.

Processing circuitry 42, 60, and/or 82 may then determine whether the estimated temperature value of electrode(s) 26 is greater than a threshold temperature value (106). The threshold temperature value may be the maximum temperature of electrode(s) 26 that may be reached during an MRI scan without undesirably heating tissue adjacent to electrodes 26. In some examples, the threshold value may be referred to as a "safe" threshold in that electrode(s) having a temperature at or below the threshold are not likely to result in undesired damage to the adjacent tissue. In some examples, the threshold value may be a temperature limit or a thermal dose limit. Thermal dose may be measured using CEM43 (cumulative equivalent minutes at 43 degrees Celsius) metric. Tissue damage threshold is different for different tissues, therefore different temperature (or thermal dose) levels may be used for different implant locations and maybe for different patient population. In some examples, CEM43 less than 30 minutes or temperature less than 43 degrees Celsius may be assumed to be "safe", however this depends on the tissue type and other factors.

If the estimated temperature of electrode(s) 26 is above the threshold value, then MRI scanner 72 may end the MRI scan to stop the RF heating and prevent electrode(s) 26 from increasing too much in temperature above the defined threshold (108). Conversely, if the estimated temperature of electrode(s) 26 is at or below the threshold value, then MRI scanner 72 may continue to deliver the MRI scan at the defined MRI settings (110). System 70 may continue to monitor the induced voltage and estimate the temperature of electrode(s) based on the induced voltage throughout the MRI scan to ensure that the estimated temperature of electrode(s) does not increase above the threshold value.

As shown in FIG. 8, in some examples, when the estimated temperature of electrode(s) 26 is determined to be at or below the threshold value (106), processing circuitry 42, 60, and/or 82 may increase the power of the MRI scan (102). While increasing the power of the scan may increase the induced voltage in lead 20 and, thus, increase the estimated temperature of electrode(s) 26, such an adjustment may be implemented so long as the estimated temperature of electrode(s) 26 does not increase above the threshold temperature value (106). In some examples, the technique of FIG. 8 may allow for an MRI scan to be carried out over a longer duration and/or at a higher power than other techniques that do not use sensed induced voltage to estimate the temperature of electrode(s) during an MRI scan.

In some examples, time average power delivered by MRI scanner 72 may be increased by increasing the power amplifier output, therefore applying higher power to the MRI coil, increasing the duration of the RF pulse, decreasing the repetition time of the RF pulse, and/or increasing the flip angle of the sequence. System 70 and/or an MRI technician or other user may change the settings to speed up an MRI scan (e.g., decrease the repetition time to shorten the overall scan duration), which may increase the average power applied to the patient.

In some examples, an MRI technician or other user may adjust scan parameters to reduce the MRI power (e.g. B1rms) to comply with IMD MRI labeling levels. B1rms labeling levels may be relatively conservative for most patients, which mean in some examples, even if B1rms is exceeded compared to MRI labeling, they may still be safe. In such cases, MRI tech may not need to alter the MRI parameters to reduce MRI power, as long as threshold induced voltage level is not reached. This provides more flexibility for the MRI tech to perform different types of scans that they want, without being unnecessarily restricted by IMD-MRI labeling levels.

In some example, in addition to, or as an alternative, to the example of FIG. 8, system 70 may be configured to display the estimate temperature of electrode(s) 26 (104) to an operator of the MRI system. For example, the estimated temperature of electrode(s) 26 (104) may be displayed to an operator via a display of user interface 84 of MRI workstation and/or user interface 66 of programmer 14. In some examples, the operator may be configured to manually control the operation of system 70 based on the displayed estimated temperature, e.g., by stopping an MRI scan when the estimated temperature of electrode(s) increases beyond a threshold value or modifying the power of the MRI scan based on the estimated temperature. In some examples, the display may continuously display the estimated temperature and the temperature may be updated in approximately real time during the MRI scan. Such a display may allow the operator to review the temperature of electrode(s) 26 during the MRI scan and make adjustments to the scan based on the estimated temperature. In some examples, user interface 84 and/or 66 may be configured to generate an alert (e.g., an audible and/or visual alert) to an operator when the estimated temperature of electrode(s) 26 is determined to be above a threshold temperature value (106).

In the example techniques of FIGS. 6-8, system 70 may be configured to initiate the detection of the voltage induced in lead 20 by the RF field generated by the MRI device upon determining that an RF field is being generated and is about to be generated by MRI scanner 72 to perform the example techniques of FIGS. 6-8. For example, processing circuitry 42 may receive a signal from the MRI device or other external device (e.g., programmer 14) instructing processing circuitry 42 to detect the voltage induced in lead 20. Such an instruction may be transmitted by external programmer 14 and/or the MRI device (e.g., MRI workstation 76 and/or scanner 72) to IMD 16, e.g., based in input from a user. Additionally, or alternatively, the MRI device and/or programmer 14 may be configured to automatically instruct IMD 16 to determine the voltage induced in lead 20 when an RF field is generated by MRI scanner 72 and/or when the MRI device receives user input initiating the one or more example techniques of FIGS. 6-8. IMD 16 may be configured to enter an "MRI mode" automatically or upon receiving instructions from the MRI device and/or programmer. In the MRI mode, IMD 16 may be configured to determine the voltage in lead 20 induced by the RF field generated by MRI scanner 72, e.g., according to the techniques of FIGS. 6-8.

As may be apparent from the disclosure, some examples of the disclosure may provide for one or more advantages. For example, examples of the disclosure may allow for an MRI scan to be performed on a patient while maintaining the temperature of electrode(s) at or below a "safe" temperature, e.g., by using induced voltage on lead 20 as a marker for RF heating. As another example, examples of the disclosure may allow for patient specific MRI power adjustments by using induced voltage on lead 20 as a marker for RF heating.

In some examples, approximately real-time monitoring of electrode temperature based on sensed voltage induced by an RF field of an MRI scan may allow for the duration of an MRI scan to be extended beyond, e.g., 30 minutes or some other non-patient specific, lead manufacturer recommended duration, if the IMD estimated electrode temperature rise is relatively low and below a "safe" threshold. In the case of relatively low power scans where the electrode temperature does not rise significantly, patient 12 patient can stay inside the MRI longer. Additionally, or alternatively, relatively high power scans beyond existing lead manufacturer recommendations may also be performed. For example, in some cases, an MRI scan for patients with implanted DBS leads may not be recommended with an RF field above 2 microTesla. However, by providing a real-time estimated temperature for electrode(s) 26 during an MRI scan, a relatively high power, short duration scan can be performed, while electrode temperature is monitored by the IMD and prevented by increasing to a temperature above a "safe" threshold. In some examples, the real-time monitoring of electrode temperature may eliminate the need or otherwise limit the need for restrictive RF field and time duration limits by IMD manufacturers.

In some examples, the techniques described herein may reduce the burden on IMD manufacturers for testing, modeling, and/or simulating MRI scan for leads using a variety of different MRI scanner to demonstrate safety of the lead for each different MRI scanner. As described above, in some examples, shimming settings of an MRI scanner 72 may be adjusted before and/or during an MRI scan to reduce the heating of electrode(s) 26 and prevent the temperature of the electrodes from increase beyond a threshold temperature. Such an approach may be used by any MRI scanner using parallel transmission arrays or multi-channel MRI coil systems (e.g., 1.5 T, 3 T, 7 T, and the like). As the MRI field moves toward more complicated transmit coils and RF/B1+ field management methods (e.g., with 4-channel transmit 3 Tesla coil or 7 Tesla Terra MRI system, using 8-channel transmit), the burden for testing/modeling/simulations to demonstrate safety may increase. As described herein, Vrms or other metric derived from sensed induced voltage can be used as a marker for RF heating, and algorithms may be developed to ensure patient safety inside MRI systems with multi-channel transmit systems.

As described herein, in some examples, IMD 16 may estimate electrode temperature in real-time throughout an MRI scan. IMD 16 may alert or stop MRI scanner 72 if a certain temperature estimation/prediction (or thermal dose) is reached to protect the patient from harm. The estimated electrode temperature may be communicated to MRI operator, displayed on the MRI workstation or other console, and/or on programmer 14. If patient 12 moves during an MRI scan, IMD 16 may detect the move from the change of induced voltage sensed by IMD 16. IMD 16 may alert MRI scanner 72 and/or MRI workstation 76, or alert the operator of the MRI device, if the patient movement or other factor has compromised the "safety" of the MRI scan, or IMD 16 may alert MRI scanner 72 and/or MRI workstation 76 in which case new shimming settings may be identified for the patient in the new position within RF transmit coil 74 of scanner 72.

As described herein, in some examples, a threshold level for the Vrms or other metric of the voltage induced in lead 20 may be used, e.g., to prevent electrode(s) 26 from increasing in temperature due to RF heating above a "safe" threshold. Such thresholds may be IMD-lead design and/or MRI frequency specific. For example, the Vrms threshold level may be lower as MRI frequency increases, because filtered feedthrough capacitors may reject a larger percentage of the incoming RF wave/pulses at higher frequencies. The Vrms threshold may be lower for shielded lead designs because a smaller amount of power may be coupled to lead electrode conductors due to presence of the shield. In some examples, lead length, insulation thickness, and electrode wire coiling might affect the Vrms threshold level. In some examples, IMD filtered feedthrough capacitance value affects the Vrms threshold level. If the capacitance is higher, a lower amount of power may be able to pass through the filter. Vrms threshold level may also be IMD 16 design specific (including lead 20) and target location specific. For different IMDs, Vrms threshold levels may need to be determined. Safe thermal dose and temperature rise levels may be different for different tissues (brain tissue, cardiac muscle, soft tissue etc.), and therefore may need to be evaluated for different therapies.

Using the examples techniques of the disclosure, IMD 16 may sense if a certain RF pulse/sequence is safe or not based on induced Vrms. IMD 16 may actively monitor the induced voltage throughout an MRI scan and predict real-time temperature rise at electrode(s) 26. IMD 16 may alert the MRI operator, MRI workstation 76, and/or MRI scanner 72 if a certain temperature or thermal dose is reached. If patient 12 moves relative to RF transmit coil 74 of scanner 72, IMD 16 may sense the change in induced voltage and generate an alert, e.g., to an operator and/or to MRI workstation 76, and/or MRI scanner 72.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory. The computer-readable storage media may be referred to as non-transitory. A programmer, such as patient programmer or clinician programmer, or other computing device may also contain a more portable removable memory type to enable easy data transfer or offline data analysis.

The techniques described in this disclosure, including those attributed to systems 10 and 70, processing circuitry 42, 60, and 82, memories 42, 62, and 80, user interfaces 66 and 84, sensing circuitry 46, and various constituent components, may be implemented, at least in part, in hardware, software, firmware or any combination thereof. For example, various aspects of the techniques may be implemented within one or more processors, formed by fixed function circuitry and/or programmable processing circuitry, including, e.g., one or more microprocessors, DSPs, ASICs, FPGAs, or any other equivalent integrated or discrete logic circuitry, as well as any combinations of such components, embodied in programmers, such as physician or patient programmers, stimulators, remote servers, or other devices. The term "processor" or "processing circuitry" may generally refer to any of the foregoing logic circuitry, alone or in combination with other logic circuitry, or any other equivalent circuitry.

As used herein, the term "circuitry" may refer to an ASIC, an electronic circuit, a processor (shared, dedicated, or group) and memory that execute one or more software or firmware programs, a combinational logic circuit, or other suitable components that provide the described functionality. The term "processing circuitry" refers one or more processors distributed across one or more devices. For example, "processing circuitry" can include a single processor or multiple processors on a device. "Processing circuitry" can also include processors on multiple devices, wherein the operations described herein may be distributed across the processors and devices.

Such hardware, software, firmware may be implemented within the same device or within separate devices to support the various operations and functions described in this disclosure. For example, any of the techniques or processes described herein may be performed within one device or at least partially distributed amongst two or more devices, such as between devices 14, 16, 72, and 77, processing circuitry 42, 60, and 82, memories 42, 62, and 80, and sensing circuitry 46. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in an article of manufacture including a non-transitory computer-readable storage medium encoded with instructions. Instructions embedded or encoded in an article of manufacture including a non-transitory computer-readable storage medium encoded, may cause one or more programmable processors, or other processors, to implement one or more of the techniques described herein, such as when instructions included or encoded in the non-transitory computer-readable storage medium are executed by the one or more processors. Example non-transitory computer-readable storage media may include RAM, ROM, programmable ROM (PROM), erasable programmable ROM (EPROM), electronically erasable programmable ROM (EEPROM), flash memory, a hard disk, a compact disc ROM (CD-ROM), a floppy disk, a cassette, magnetic media, optical media, or any other computer readable storage devices or tangible computer readable media.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache). Elements of devices and circuitry described herein, including, but not limited to, devices 14, 16, 72, and 77, processing circuitry 42, 60, and 82, memories 42, 62, and 80, and sensing circuitry 46 may be programmed with various forms of software. The one or more processors may be implemented at least in part as, or include, one or more executable applications, application modules, libraries, classes, methods, objects, routines, subroutines, firmware, and/or embedded code, for example.

In examples in which processing circuitry 42, 60, and 82 is described herein as determining that a value is less than or equal to another value, processing circuitry 42, 60, and 82 may be configured to determine that a value is only less than the other value. Similarly, in examples in which processing circuitry 42, 60, and 82 is described herein as determining that a value is less than another value, processing circuitry 42, 60, and 82 may be configured to determine that a value is less than or equal to the other value. The same properties may also apply to the terms "greater than" and "greater than or equal to."

EXAMPLES

As series of tests were performed to evaluate one or more aspects of some examples of the disclosure. However, the disclosure is not limited by the tests.

A first test was performed to evaluate the use of different shimming settings for an MRI scan and the influence on induced voltage and temperature increase in an implanted lead. An MRI scan with a 3 T MRI scanner was modeled for a patient having an IMD including a conductive lead and electrode implanted in the pelvic floor of the patient near the sacral nerve. The modeling was performed to evaluate the induced voltage and resulting temperature increase in the lead and electrode for a variety of possible MRI scan settings. The induced voltage and temperature increase were calculated using a Tier 3 transfer function approach as defined in ISO/TS 10974 edition 2, 2018.

Figure 9:
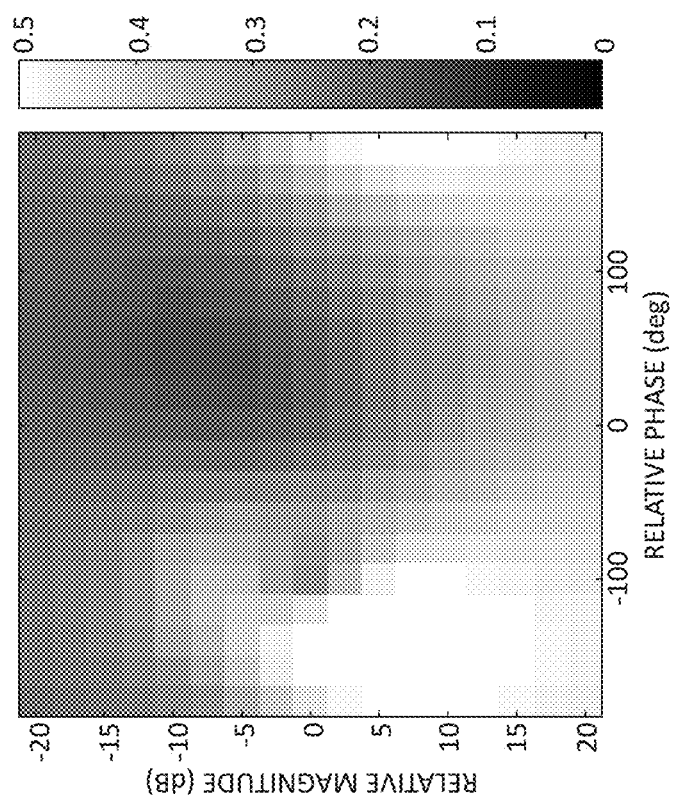
FIGS. 9-19 are various images and plots relative to a series of tests that were performed to evaluate one or more aspect of some examples of the disclosure.
Figure 10:
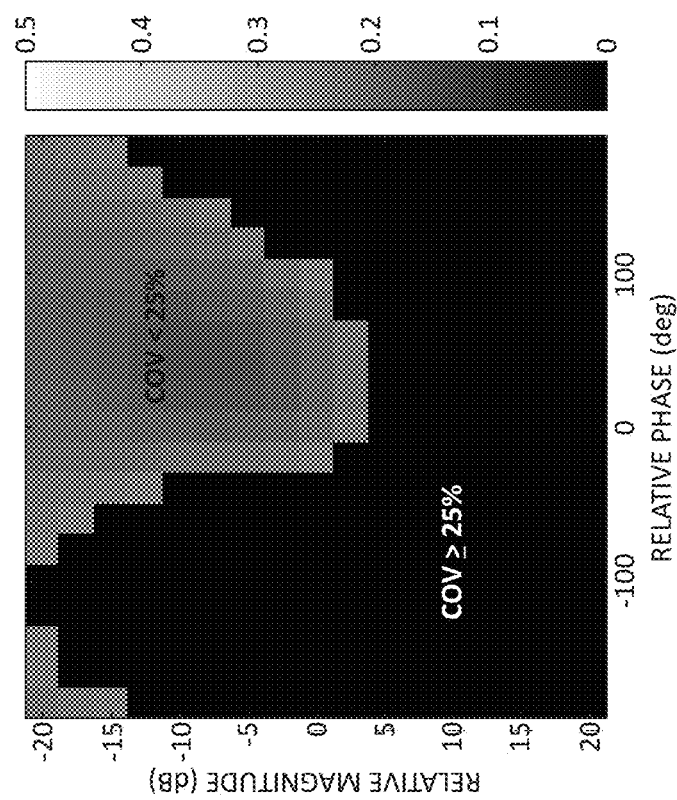

FIG. 9 is a plot illustrating the circularly-polarized magnetic field (B1+) distribution calculated for different 3 T MRI shimming settings by varying relative magnitude and relative phase of the multielement RF coil of the MRI scanner. More specifically, FIG. 9 shows the coefficient of variation (COV) of the B1+ distribution for different relative magnitude and phases between channel 1 and channel 2 of a two-channel transmit MRI RF coil. FIG. 10 is plot illustrating the shimming settings having a coefficient of variation calculated as having a COV of less than 25% versus a COV of equal to or greater than 25%. More specifically, FIG. 10 shows the same results as FIG. 9 except that COV greater than or equal to 25% are masked out with a darker shading. COV is standard deviation of the magnetic field magnitude divided by its mean, therefore smaller numbers indicate that magnetic field distribution is more uniform. A COV of less than 25% was used as clinical relevance criterion for the evaluation of the shimming settings but it was recognized that other COV greater or less than 25% may also be useful in evaluating shimming settings.

Figure 11B:
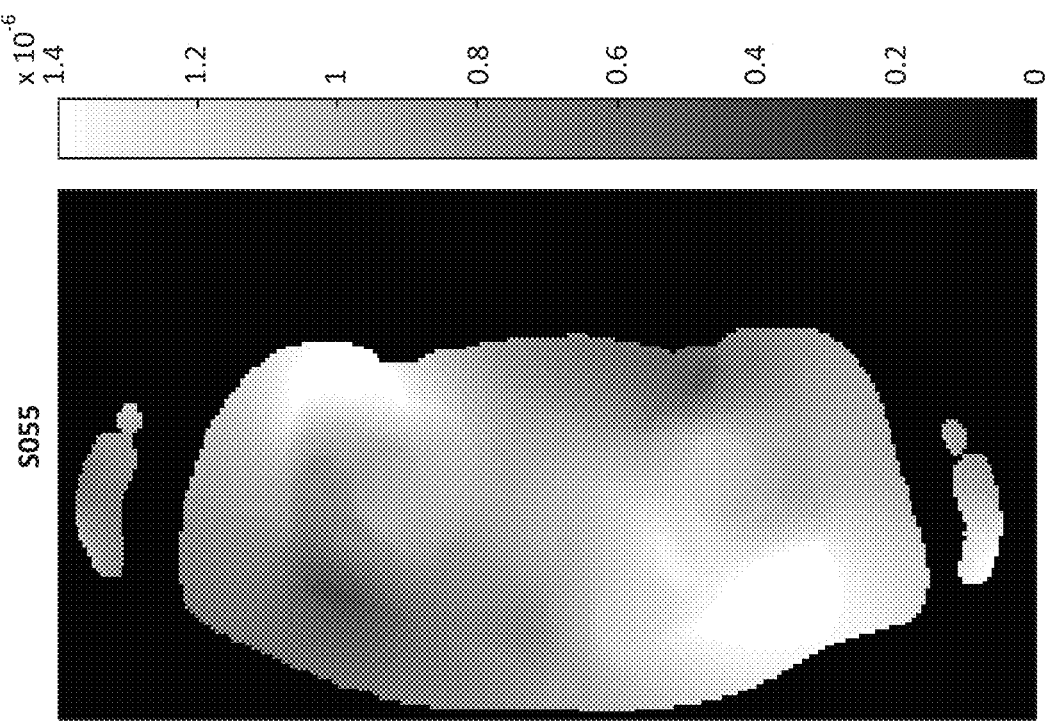
Figure 11A:
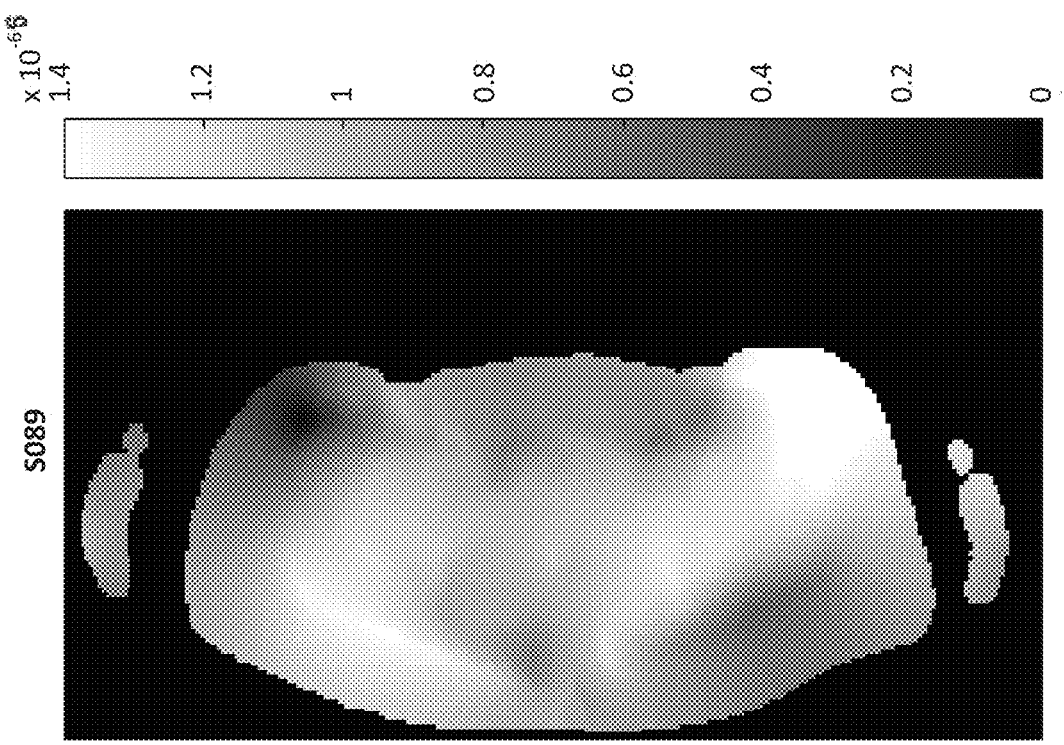

FIGS. 11A and 11B are plots of the calculated magnetic field distribution within the same anatomical location of the patient for two different MRI shimming settings S089 and S055, respectively. The shimming settings for each were (assuming that channel 1 was the nominal channel and reporting the relative magnitude and phase of channel 2 compared to channel 1) S055: −12.5 dB, 160 degrees (12.5 dB lower magnitude); and S089: 0 dB, −20 degrees (same magnitude). As shown, in some areas, the magnetic field may be relatively similar in some anatomical locations and may provide similar MRI scan performance in those anatomical locations.

Figure 12A:
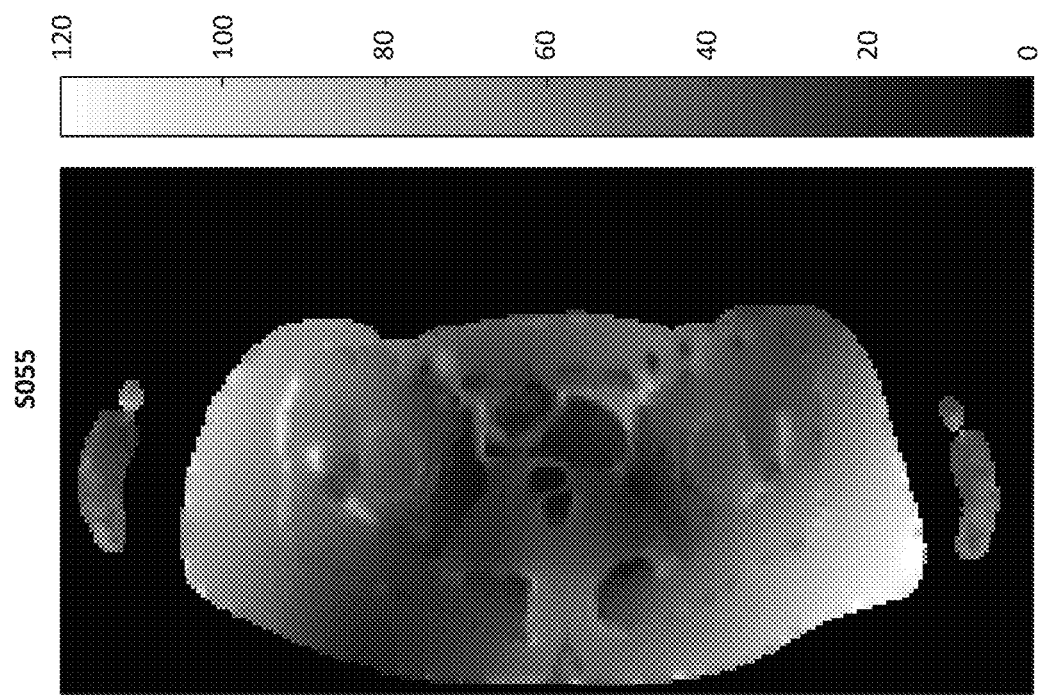
Figure 12B:
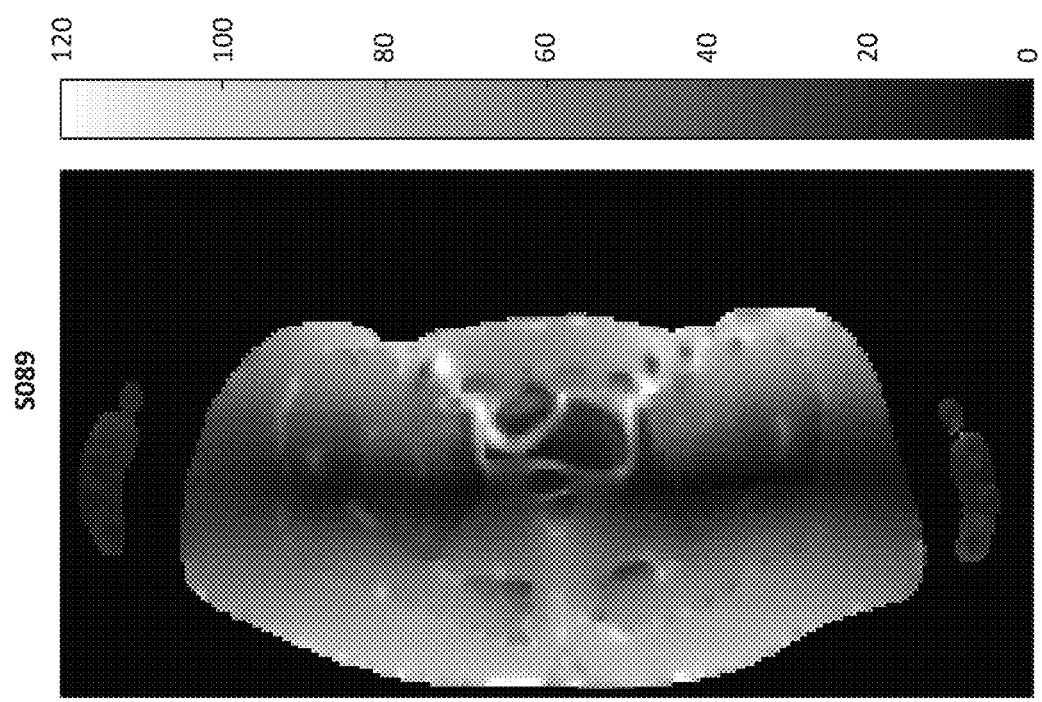

FIGS. 12A and 12B are plots of the calculated electric field distribution within the same anatomical location of the patient for the two different MRI shimming settings S089 and S055, respectively, of FIGS. 11A and 11B. The plots of FIGS. 11A-12B demonstrated that the two shim setting may each provide suitable magnetic fields for MRI in the same anatomical locations while providing different electric field distributions.

Figure 13:
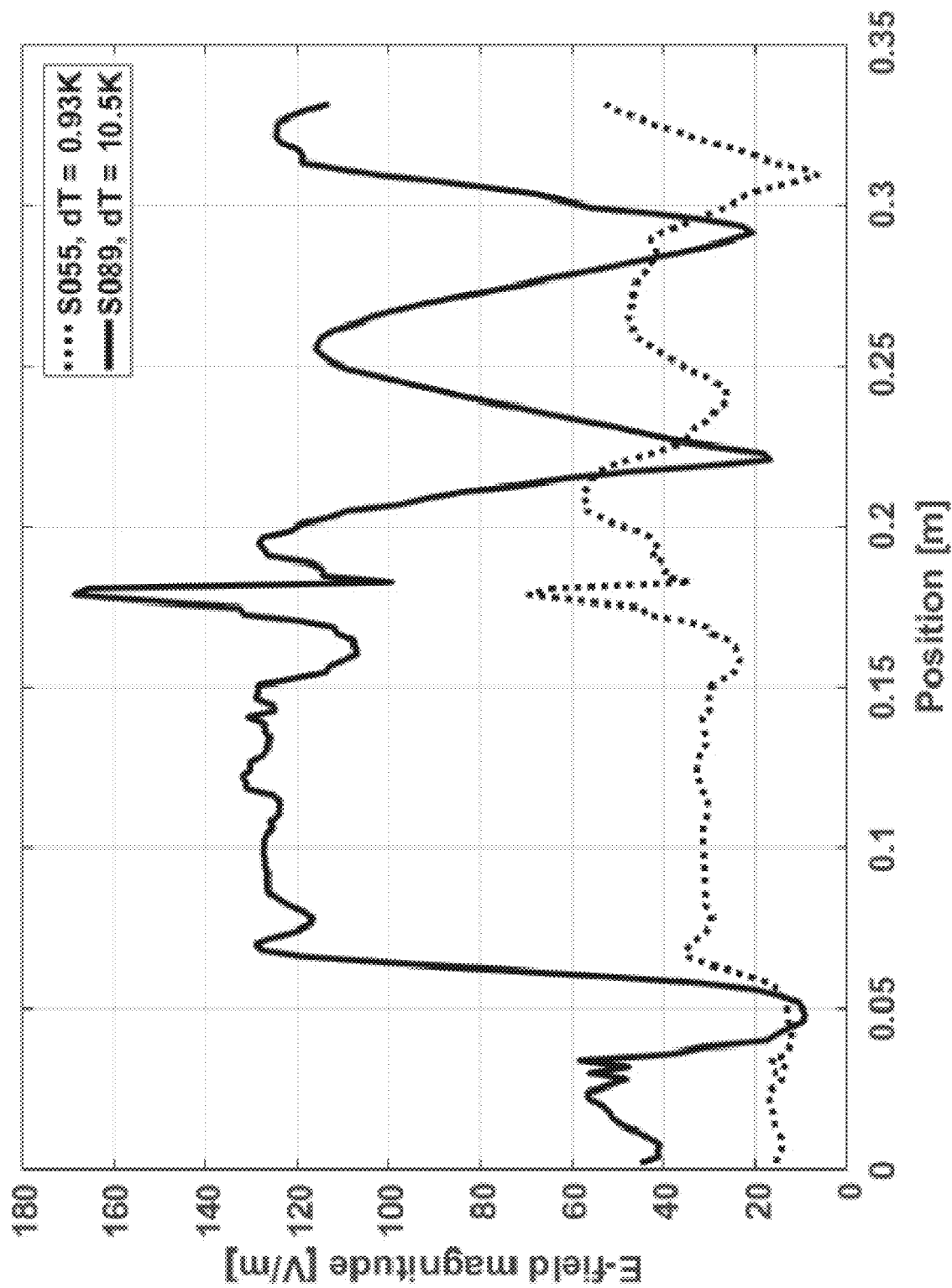

FIG. 13 is a plot showing the electric field distribution magnitude (volts/meter (V/m)) versus position along the length of the modeled lead calculated for each shimming setting (S089 and S055) for a selected implant path of the lead. Using the modeled values, the induced voltage in terms of Vrms in the lead and temperature increase (dT) of the conductive lead with the induced voltage was calculated for each shimming setting. Incident E-field along the lead due to shim setting S089 was on average higher than the E-field due to shim setting S055. For shimming setting S089, the calculated Vrms was 301 millivolts and the dT was 10.5 Kelvin (K). For shimming setting S055, the calculated Vrms was 91 millivolts and the dT was 0.9 K.

Figure 14:
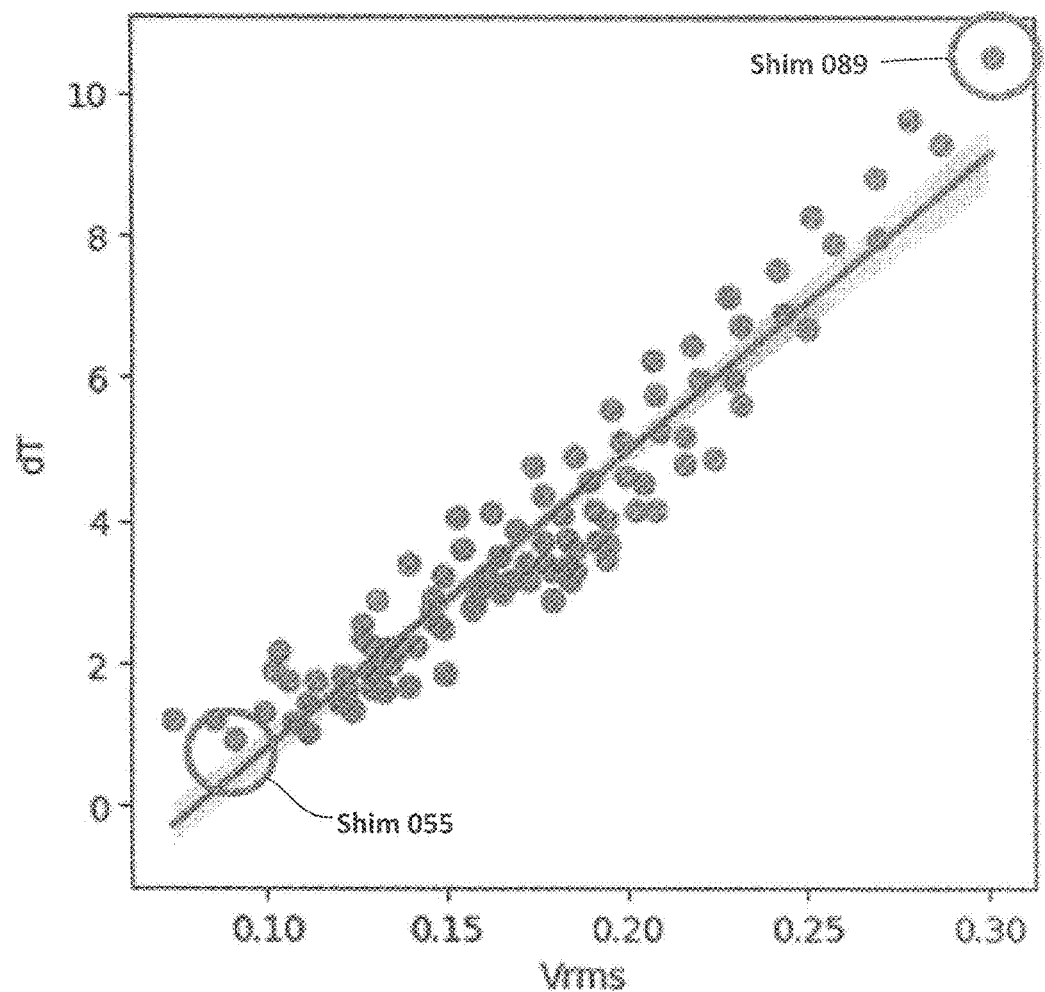

The same calculations were made for a plurality of other shimming settings with the same lead along the same implant path used for FIG. 13. FIG. 14 is a plot of temperature increase (dT) versus induced voltage in terms of Vrms for each of the different shimming settings, including shimming settings 089 and 055. As shown, there was a substantially linear relationship between induced voltage and dT for the lead calculated for the different shimming settings. Shimming setting 055 resulted in one of the lowest Vrms and dT of all the modeled shimming settings. Shimming setting 089 resulted in one of the highest Vrms and dT of all the modeled shimming settings.

The plots of FIGS. 13-14 demonstrated that there may be a strong positive correlation between the induced voltage and temperature rise and thus, induced voltage was determined to be an appropriate marker to predict RF heating.

Figure 15:
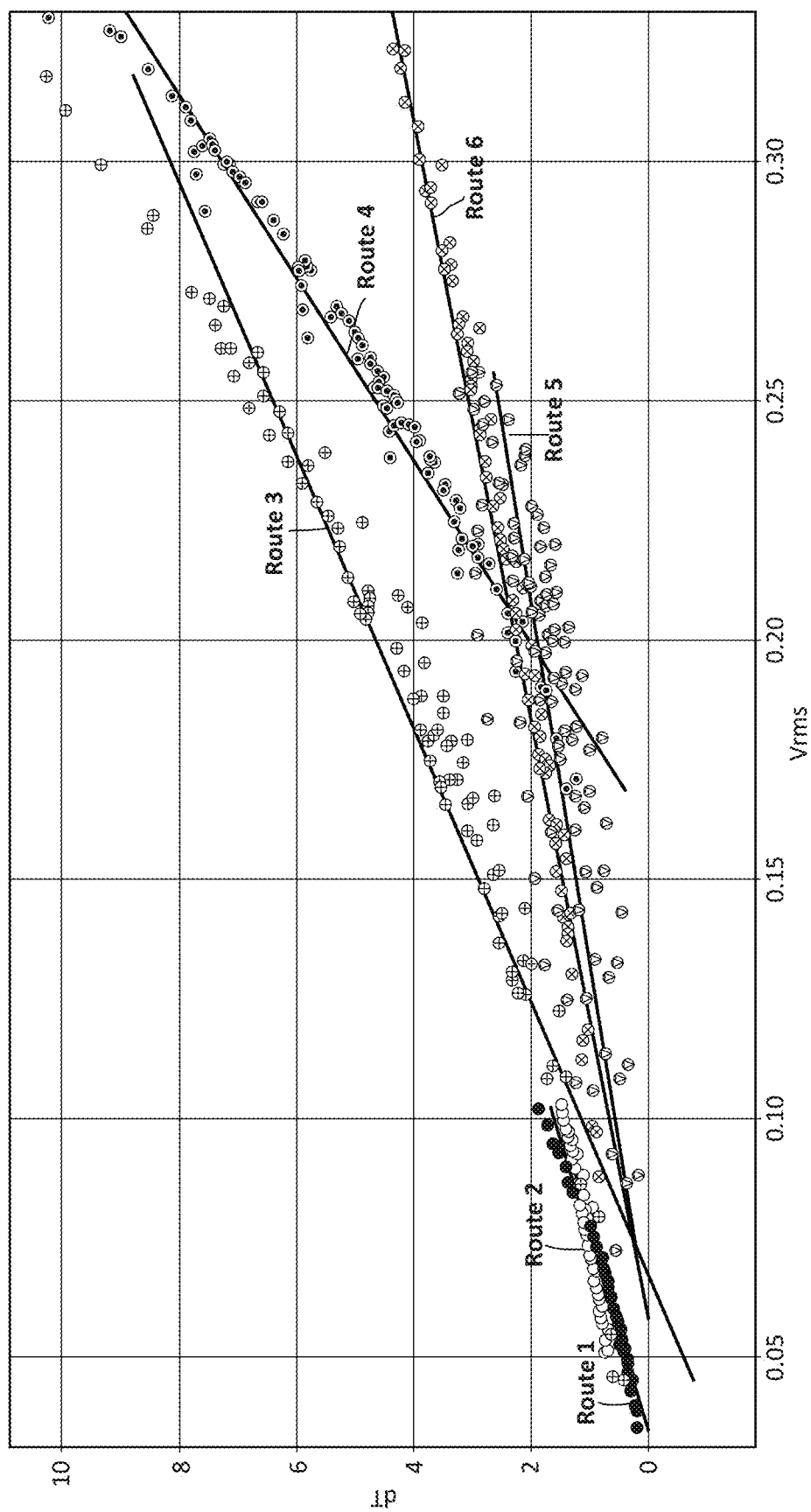

The same process used to generate the plots of FIGS. 13 and 14 was used to calculate the Vrms and dT for the same shimming settings for a plurality of different lead implant routes. FIG. 15 is a plot of Vrms and dT calculated for six of the different lead implant routes with those shimming settings. As demonstrated by FIG. 15, there was a strong correlation between induced voltage (Vrms) and RF heating for a number of different lead routing paths.

In a second test, the use of induced voltage in a lead by an RF field of an MRI scan as a marker of electrode heating was evaluated. Two different multiple linear regression predictive models for estimating temperature increase in an implanted lead during an MRI were used for the evaluation. The models were used to estimate lead heating during a 1.5 T MRI scan on a variety of patients. Each patient had a lead implanted to deliver sacral nerve stimulation with electrodes.

The first model (Model 1) used input parameters that did not include induced voltage in terms of Vrms. The particular input parameters were patient height, patient weight, implant lead length, landmark (LM) value, MRI RF coil length, MRI RF coil diameter, circularly-polarized excitation orientation (clockwise or counter-clockwise orientation), target stimulation site (S4 or S3 nerve), side of patient spinal column that the lead was implanted (left or right side of spinal column), and side of patient spinal column that the IMD housing was implanted (left or right side of spinal column). LM refers to the position of the patient inside the MRI scanner in z-axis (e.g. a parameter to describe scan location, head scan, cardiac scan, knee scan etc). In the first model, LM was 0 at the top of the head of the patient and the LM value increased toward the feet (e.g. LM=30 cm was at approximately the shoulders of the patient, LM=100 cm was at approximately the pelvis of the patient, and so forth).

The second model (Model 2) used the same input parameters as Model 1 but also included sensed induced voltage in the lead in the context of Vrms as an input parameter. The voltage was calculated using a Tier 3 transfer function approach as defined in ISO/TS 10974 edition 2, 2018.

Figure 16:
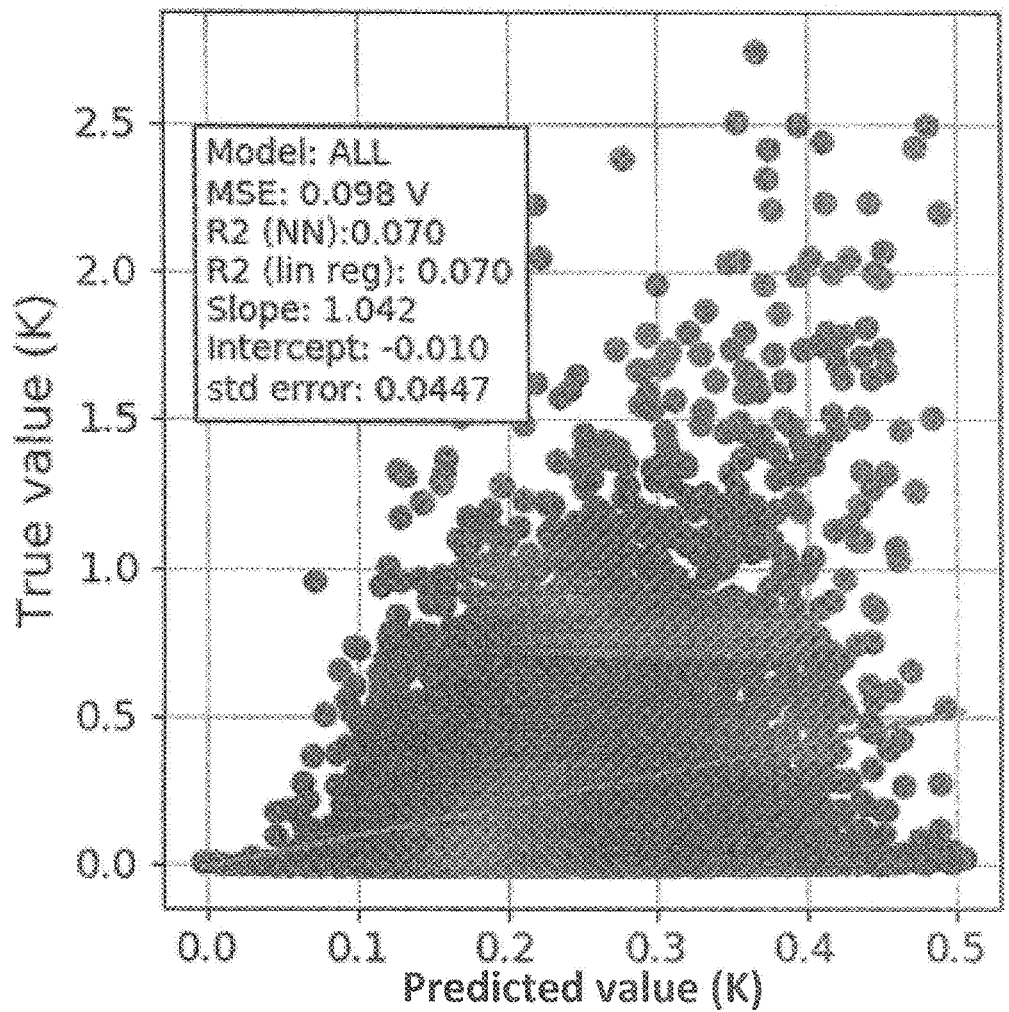

For each patient, electrode heating was predicted using Model 1 and Model 2. The estimated electrode heating was then compared to the actual electrode heating measured for each patient for the modeled MRI scan. FIG. 16 is a plot of the actual electrode temperature increase (True Value (K)) versus electrode temperature increase estimated using Model 1. For comparison, FIG. 17 is a plot of the actual electrode temperature increase (True Value (K)) versus estimated electrode temperature increase predicted using Model 2.

Two additional models (Model 3 and Model 4) were also used to estimate electrode heating for the same MRI scans. Model 3 used the same input parameters as Model 1, and Model 4 used the same input parameters of Model 2. Unlike that of the multiple linear regression models of Model 1 and Model 2, Model 3 and Model 4 used artificial neural network architecture. The dataset was partitioned into training and test sets. The artificial neural network predictive models (Model 3 and 4) had two hidden layers with 60 units in each layer. The artificial neural network predictive model parameters (Model 3 and Model 4) were trained using the training set. Then the performance of the artificial neural network models was tested using the test set.

FIG. 18 is a plot of the actual electrode temperature increase (True Value (K)) versus electrode temperature increase predicted using Model 3. For comparison, FIG. 19 is a plot of the actual electrode temperature increase (True Value (K)) versus electrode temperature increase predicted using Model 4.

As demonstrated by the results shown in FIGS. 16-19, the predictive modeling including the sensed induced voltage (Vrms) in the lead as an input parameter to predict electrode heating during a 1.5 T MRI scan significantly overperformed the predictive models that did not use sensed induced voltage. For example, the models using induced voltage (Vrms) as an input parameter were determined to be more accurate, e.g., as demonstrated by the model performance metrics are included in each plot. In the plots, MSE refers to mean-squared error where lower values are better, and R2 refers to R-squared metric where higher values are better. Comparing the MSE and R2 between the different models showed that models including induced voltage as an input parameter were more accurate in predicting RF heating. Furthermore, FIGS. 16-19 demonstrated that, in some cases, more sophisticated predictive algorithms (e.g. neural networks) may perform better compared to simpler algorithms (e.g. multiple linear regression).

Various examples of the disclosure have been described. Any combination of the described systems, operations, or functions is contemplated. These and other examples are within the scope of the following claims and clauses.

Clause 1. A method comprising detecting, via processing circuitry, an induced voltage in at least one of an electrode or a lead conductor of an implantable medical device, wherein the induced voltage is induced in the at least one of the electrode or the lead conductor of the implantable medical device by a radio frequency (RF) field generated by a magnetic resonance imaging (MRI) scanner; and modifying, via the processing circuitry, an MRI scan based on the detected induced voltage.

Clause 2. The method of clause 1, wherein modifying the MRI scan based on the detected induced voltage comprises modifying an electric field distribution of the MRI scan based on the detected induced voltage.

Clause 3. The method of clause 2, wherein modifying an electric field distribution of the MRI scan based on the detected induced voltage comprises adjusting a shimming setting of the MRI scan based on the detected induced voltage.

Clause 4. The method of clause 1, wherein detecting the induced voltage from in the at least one of the electrode or the lead conductor of the implantable medical device comprises determining a magnitude of the induced voltage, the method further comprising determining the magnitude of the induced voltage is greater than a threshold value, wherein modifying the MRI scan based on the detected induced voltage comprises modifying the MRI scan based on the determination that the magnitude of the induced voltage is greater than the threshold value.

Clause 5. The method of clause 1, wherein modifying the MRI scan based on the detected induced voltage comprises terminating the MRI scan based on the detected induced voltage.

Clause 6. The method of clause 1, wherein modifying the MRI scan based on the detected induced voltage comprises continuing the MRI scan based on the detected induced voltage.

Clause 7. The method of clause 1, wherein modifying the MRI scan based on the detected induced voltage comprises increasing a power of the MRI scan based on the detected induced voltage.

Clause 8. The method of clause 1, wherein detecting the induced voltage in the at least one of the electrode or the lead conductor of the implantable medical device comprises determining a root mean square voltage value for the induced voltage.

Clause 9. The method of clause 1, further comprising predicting a temperature of the at least one of the electrode or the lead conductor of the implantable medical device based on the detected induced voltage.

Clause 10. The method of clause 9, further comprising displaying the predicted temperature via a display.

Clause 11. The method of clause 9, wherein modifying the MRI scan based on the detected induced voltage comprises modifying the MRI scan based on the predicted temperature.

Clause 12. The method of clause 1, wherein detecting the induced voltage comprises receiving, with an MRI device configured to control the MRI scan, information for the induced voltage from the implantable medical device, the method further comprising sensing the induced voltage using one or more electrodes of the implantable medical device.

Clause 13. The method of clause 1, wherein the induced voltage is induced in the lead conductor of the medical device.

Clause 14. The method of clause 1, wherein the induced voltage is induced in the electrode of the implantable medical device.

Clause 15. The method of clause 14, wherein the induced voltage is induced at a tissue interface of the electrode.

Clause 16. The method of clause 1, further comprising delivering the RF field generated by the MRI scanner.

Clause 17. A system comprising an implantable medical device; a magnetic resonance imaging (MRI) scanner; and processing circuitry, wherein the implantable medical device is configured to detect an induced voltage in at least one of an electrode or a lead conductor of the implantable medical device, wherein the induced voltage is induced in the at least one of the electrode or the lead conductor of the implantable medical device by a radio frequency (RF) field generated by a magnetic resonance imaging (MRI) scanner, and modify an MRI scan based on the detected induced voltage.

Clause 18. The system of clause 17, wherein the processing circuitry is configured to modify an electric field distribution of the MRI scan based on the detected induced voltage.

Clause 19. The system of clause 18, wherein the processing circuitry is configured to adjust a shimming setting of the MRI scan based on the detected induced voltage.

Clause 20. The system of clause 17, wherein the processing circuitry is configured to determine a magnitude of the induced voltage, determine the magnitude of the induced voltage is greater than a threshold value, and modify the MRI scan based on the determination that the magnitude of the induced voltage is greater than the threshold value.

Clause 21. The system of clause 17, wherein the processing circuitry is configured to terminate the MRI scan based on the detected induced voltage.

Clause 22. The system of clause 17, wherein the processing circuitry is configured to control the MRI scanner to continue the MRI scan based on the detected induced voltage.

Clause 23. The system of clause 17, wherein the processing circuitry is configured to increase a power of the MRI scan based on the detected induced voltage.

Clause 24. The system of clause 17, wherein the processing circuitry is configured to determine a root mean square voltage value for the induced voltage.

Clause 25. The system of clause 17, wherein the processing circuitry is configured to predict a temperature of the at least one of the electrode or the lead conductor of the implantable medical device based on the detected induced voltage.

Clause 26. The system of clause 25, further comprising a display device, wherein the processing circuitry is configured to display, via the display device, the predicted temperature.

Clause 27. The system of clause 25, wherein the processing circuitry is configured to modify the MRI scan based on the predicted temperature.

Clause 28. The system of clause 17, wherein the processing circuitry is configured to receive, with an MRI device configured to control the MRI scan, information for the induced voltage from the implantable medical device, and sense the induced voltage using one or more electrodes of the implantable medical device.

Clause 29. The system of clause 17, wherein the induced voltage is induced in the lead conductor of the medical device.

Clause 30. The system of clause 17, wherein the induced voltage is induced in the electrode of the implantable medical device.

Clause 31. The system of clause 30, wherein the induced voltage is induced at a tissue interface of the electrode.

Clause 32. The system of clause 17, wherein the processing circuitry is configured to control the delivery the RF field generated by the MRI scanner.

Clause 33. A method comprising sensing, via an implantable medical device, an induced voltage in at least one of an electrode or a lead conductor of the implantable medical device, wherein the induced voltage is induced in the at least one of the electrode or the lead conductor of the implantable medical device by a radio frequency (RF) field generated by a magnetic resonance imaging (MRI) scanner; and transmitting, from the implantable medical device to an MRI device, at least one of voltage information defined by the sensed induced voltage information or control information including instructions for controlling the MRI scanner to deliver an MRI scan based on the sensed induced voltage.

Clause 34. The method of clause 33, wherein the implantable medical device includes the electrode and the lead conductor, wherein sensing the induced voltage in the at least one of the electrode or the lead conductor of the implantable medical device comprises sensing the induced voltage in the lead conductor of the implantable medical device, and wherein the induced voltage in the lead conductor increases a temperature of the electrode.

Clause 35. The method of clause 34, further comprising at least one of delivering electrical stimulation therapy to a patient via the electrode and conductive lead or sensing bioelectrical signals of the patient via the electrode and conductive lead.

Clause 36. The method of clause 33, wherein the instructions for controlling the MRI scanner to deliver an MRI scan based on the sensed induced voltage include a modification to the MRI scan based on the detected induced voltage.

Clause 37. The method of clause 36, wherein the modification to the MRI scan based on the detected induced voltage comprise a modification to the shimming settings for the RF field generated by the MRI scanner.

Clause 38. The method of clause 36, wherein the modification to the MRI scan based on the detected induced voltage comprise a modification to an electric field distribution of the MRI scan based on the detected induced voltage.

Clause 39. The method of clause 36, wherein the modification to the MRI scan based on the detected induced voltage comprise termination of the MRI scan based on the detected induced voltage.

Clause 40. The method of clause 36, wherein the modification to the MRI scan based on the detected induced voltage comprise an increase in a power of the MRI scan based on the detected induced voltage.

Clause 41. The method of clause 33, further comprising determining, via the processing circuitry, a root mean square voltage value for the induced voltage, wherein the voltage information defined by the sensed induced voltage information comprises the root mean square voltage value.

Clause 42. The method of clause 33, further comprising predicting a temperature of the implantable medical device based on the detected induced voltage.

Clause 43. The method of clause 42, wherein the instructions for controlling the MRI scanner to deliver an MRI scan based on the sensed induced voltage include a modification to the MRI scan based on the predicted temperature of the implantable medical device.

Clause 44. The method of clause 33, further comprising detecting, with the implantable medical device, activation of an MRI scan, wherein the MRI scanner generates the RF field during the MRI scan, and wherein sensing the induced voltage in the at least one of the electrode or the lead conductor of the implantable medical device comprises sensing, in response to the detection, the induced voltage in the at least one of the electrode or the lead conductor of the implantable medical device.

Clause 45. The method of clause 44, wherein detecting, with the implantable medical device, activation of the MRI scan comprises receiving, from an external device to the implantable medical device, a signal indicating the activation of the MRI scan.

Clause 46. The method of clause 45, wherein the external device comprises an external programmer device.

Clause 47. A system comprising an implantable medical device; and processing circuitry, wherein the processing circuitry is configured to sense, via the implantable medical device, an induced voltage in at least one of an electrode or a lead conductor of the implantable medical device, wherein the induced voltage is induced in the at least one of the electrode or the lead conductor of the implantable medical device by a radio frequency (RF) field generated by a magnetic resonance imaging (MRI) scanner, and transmit, from the implantable medical device to an MRI device, at least one of voltage information defined by the sensed induced voltage information or control information including instructions for controlling the MRI scanner to deliver an MRI scan based on the sensed induced voltage.

Clause 48. The system of clause 47, wherein the implantable medical device includes the electrode and the lead conductor, wherein the processing circuitry is configured to sense the induced voltage in the lead conductor of the implantable medical device, and wherein the induced voltage in the lead conductor increases a temperature of the electrode.

Clause 49. The system of clause 48, wherein the implantable medical device is configured to deliver electrical stimulation therapy to a patient via the electrode and the conductive lead or sensing bioelectrical signals of the patient via the electrode and the conductive lead.

Clause 50. The system of clause 47, wherein the instructions for controlling the MRI scanner to deliver an MRI scan based on the sensed induced voltage include a modification to the MRI scan based on the detected induced voltage.

Clause 51. The system of clause 50, wherein the modification to the MRI scan based on the detected induced voltage comprise a modification to the shimming settings for the RF field generated by the MRI scanner.

Clause 52. The system of clause 50, wherein the modification to the MRI scan based on the detected induced voltage comprise a modification to an electric field distribution of the MRI scan based on the detected induced voltage.

Clause 53. The system of clause 50, wherein the modification to the MRI scan based on the detected induced voltage comprise termination of the MRI scan based on the detected induced voltage.

Clause 54. The system of clause 50, wherein the modification to the MRI scan based on the detected induced voltage comprise an increase in a power of the MRI scan based on the detected induced voltage.

Clause 55. The system of clause 47, wherein the processing circuitry is configured to determine a root mean square voltage value for the induced voltage, and wherein the voltage information defined by the sensed induced voltage information comprises the root mean square voltage value.

Clause 56. The system of clause 47, wherein the processing circuitry is configured to predict a temperature of the implantable medical device based on the detected induced voltage.

Clause 57. The system of clause 56, wherein the instructions for controlling the MRI scanner to deliver an MRI scan based on the sensed induced voltage include a modification to the MRI scan based on the predicted temperature of the implantable medical device.

Clause 58. The system of clause 47, wherein the processing circuitry is configured to detect, with the implantable medical device, activation of an MRI scan, wherein the MRI scanner generates the RF field during the MRI scan, and the processing circuitry is configured to sense, in response to the detection, the induced voltage in the at least one of the electrode or the lead conductor of the implantable medical device.

Clause 59. The system of clause 58, wherein the processing circuitry is configured to receive, from an external device to the implantable medical device, a signal indicating the activation of the MRI scan.

Clause 60. The system of clause 59, wherein the external device comprises an external programmer device.

Clause 61. A method comprising means for detecting, via processing circuitry, an induced voltage in at least one of an electrode or a lead conductor of an implantable medical device, wherein the induced voltage is induced in the at least one of the electrode or the lead conductor of the implantable medical device by a radio frequency (RF) field generated by a magnetic resonance imaging (MRI) scanner; and means for modifying, via the processing circuitry, an MRI scan based on the detected induced voltage.

Clause 62. A method comprising means for sensing, via an implantable medical device, an induced voltage in at least one of an electrode or a lead conductor of the implantable medical device, wherein the induced voltage is induced in the at least one of the electrode or the lead conductor of the implantable medical device by a radio frequency (RF) field generated by a magnetic resonance imaging (MRI) scanner; and means for transmitting, from the implantable medical device to an MRI device, at least one of voltage information defined by the sensed induced voltage information or control information including instructions for controlling the MRI scanner to deliver an MRI scan based on the sensed induced voltage.

The invention claimed is:

1. A method comprising:
   detecting, by first processing circuitry of an implantable medical device disposed completely within a patient, an induced voltage in at least one of an electrode or a lead conductor of an implantable medical device, wherein the induced voltage is induced in the at least one of the electrode or the lead conductor of the implantable medical device by a radio frequency (RF) field generated by a magnetic resonance imaging (MRI) scanner;
   predicting a temperature of the at least one of the electrode or the lead conductor of the implantable medical device based on the detected induced voltage;
   transmitting, by the implantable medical device, information indicative of the induced voltage to second processing circuitry; and
   modifying, by the second processing circuitry, an MRI scan parameter setting based on the detected induced voltage.

2. The method of claim 1, wherein modifying the MRI scan parameter setting based on the detected induced voltage comprises modifying an electric field distribution of the MRI scan based on the detected induced voltage, wherein modifying the electric field distribution of the MRI scan based on the detected induced voltage comprises modifying at least one of a magnitude or a phase of an RF wave of the MRI scan.

3. The method of claim 2, wherein modifying an electric field distribution of the MRI scan parameter setting based on the detected induced voltage comprises adjusting a shimming setting of the MRI scan based on the detected induced voltage.

4. The method of claim 1, wherein detecting the induced voltage from in the at least one of the electrode or the lead conductor of the implantable medical device comprises determining a magnitude of the induced voltage, the method further comprising:
   determining the magnitude of the induced voltage is greater than a threshold value,
   wherein modifying the MRI scan parameter setting based on the detected induced voltage comprises modifying the Mill scan based on the determination that the magnitude of the induced voltage is greater than the threshold value.

5. The method of claim 1, wherein modifying the Mill scan parameter setting based on the detected induced voltage comprises terminating the MRI scan based on the detected induced voltage.

6. The method of claim 1, wherein modifying the Mill scan parameter setting based on the detected induced voltage comprises continuing the Mill scan based on the detected induced voltage.

7. The method of claim 1, wherein modifying the Mill scan parameter setting based on the detected induced voltage comprises at least one of increasing or decreasing a power of the MRI scan based on the detected induced voltage.

8. The method of claim 1, wherein detecting the induced voltage in the at least one of the electrode or the lead conductor of the implantable medical device comprises determining a root mean square voltage value for the induced voltage.

9. The method of claim 1, further comprising displaying the predicted temperature via a display.

10. The method of claim 1, wherein predicting a temperature of the at least one electrode comprises estimating the temperature in an implanted lead using a linear regression predictive model.

11. The method of claim 1, wherein modifying the MRI scan parameter setting comprises modifying the MRI scan parameter setting based on the temperature of the at least one of the electrode or the lead conductor of the implantable medical device.

12. A system comprising:
an implantable medical device configured to be completely disposed within a patient;
a magnetic resonance imaging (MRI) scanner; and
processing circuitry, wherein the implantable medical device is, via the processing circuitry, configured to:
detect an induced voltage in at least one of an electrode or a lead conductor of the implantable medical device, wherein the induced voltage is induced in the at least one of the electrode or the lead conductor of the implantable medical device by a radio frequency (RF) field generated by a magnetic resonance imaging (MRI) scanner,
predict a temperature of the at least one of the electrode or the lead conductor of the implantable medical device based on the detected induced voltage,
and modify an MRI scan parameter setting based on the detected induced voltage.

13. The system of claim 12, wherein the processing circuitry is configured to modify an electric field distribution of the MRI scan based on the detected induced voltage, wherein modification of the electric field distribution of the MRI scan based on the detected induced voltage comprises modification of at least one of a magnitude or a phase of an RF wave of the MRI scan.

14. The system of claim 13, wherein the processing circuitry is configured to adjust a shimming setting of the MRI scan based on the detected induced voltage.

15. The system of claim 12, wherein the processing circuitry is configured to determine a magnitude of the induced voltage, determine the magnitude of the induced voltage is greater than a threshold value, and modify the MRI scan parameter setting based on the determination that the magnitude of the induced voltage is greater than the threshold value.

16. The system of claim 12, wherein the processing circuitry is configured to terminate the MRI scan based on the detected induced voltage.

17. The system of claim 12, wherein the processing circuitry is configured to control the MRI scanner to continue the MRI scan based on the detected induced voltage.

18. The system of claim 12, wherein the processing circuitry is configured to at least one of increase or decrease a power of the MRI scan based on the detected induced voltage.

19. The system of claim 12, wherein the processing circuitry is configured to determine a root mean square voltage value for the induced voltage.

20. The system of claim 12, further comprising a display device, wherein the processing circuitry is configured to display, via the display device, the predicted temperature.

21. The system of claim 12, wherein the processing circuitry is configured to modify the MRI scan parameter setting based on the temperature of the at least one of the electrode or the lead conductor of the implantable medical device.

22. A method comprising:
sensing, by an implantable medical device disposed completely within a patient, an induced voltage in at least one of an electrode or a lead conductor of the implantable medical device, wherein the induced voltage is induced in the at least one of the electrode or the lead conductor of the implantable medical device by a radio frequency (RF) field generated by a magnetic resonance imaging (MRI) scanner;
predicting a temperature of the at least one of the electrode or the lead conductor of the implantable medical device based on the sensed induced voltage; and
transmitting, from the implantable medical device to an MRI device, at least one of voltage information defined by the sensed induced voltage information or control information including instructions for controlling the MRI scanner to deliver an MRI scan based on the sensed induced voltage.

23. A system comprising:
an implantable medical device configured to be disposed completely within a patient; and
processing circuitry configured to:
sense, via the implantable medical device, an induced voltage in at least one of an electrode or a lead conductor of the implantable medical device, wherein the induced voltage is induced in the at least one of the electrode or the lead conductor of the implantable medical device by a radio frequency (RF) field generated by a magnetic resonance imaging (MRI) scanner,
predict a temperature of the at least one of the electrode or the lead conductor of the implantable medical device based on the sensed induced voltage; and
transmit, from the implantable medical device to an MRI device, at least one of voltage information defined by the sensed induced voltage or control information including instructions for controlling the MRI scanner to deliver an MRI scan based on the sensed induced voltage.

* * * * *